United States Patent
Takemoto et al.

(10) Patent No.: US 9,073,823 B2
(45) Date of Patent: Jul. 7, 2015

(54) COMPOUND HAVING HETERO RING SKELETON, AND PROCESS FOR PRODUCING OPTICALLY ACTIVE COMPOUND USING THE AFOREMENTIONED COMPOUND AS ASYMMETRIC CATALYST

(71) Applicants: Yoshiji Takemoto, Kyoto (JP); Kazuo Murakami, Kashiba (JP)

(72) Inventors: Yoshiji Takemoto, Kyoto (JP); Kazuo Murakami, Kashiba (JP)

(73) Assignees: Kyoto University, Kyoto (JP); Sumitomo Chemical Company, Limited, Tokyo (JP)

( * ) Notice: Subject to any disclaimer, the term of this patent is extended or adjusted under 35 U.S.C. 154(b) by 18 days.

(21) Appl. No.: 13/828,411

(22) Filed: Mar. 14, 2013

(65) Prior Publication Data

US 2013/0245257 A1 Sep. 19, 2013

Related U.S. Application Data

(62) Division of application No. 13/259,887, filed as application No. PCT/JP2010/056463 on Apr. 9, 2010, now Pat. No. 8,580,804.

(30) Foreign Application Priority Data

Apr. 10, 2009 (JP) .................................. 2009-096449

(51) Int. Cl.
| | |
|---|---|
| *C07C 253/30* | (2006.01) |
| *C07B 53/00* | (2006.01) |
| *C07C 67/343* | (2006.01) |
| *C07C 205/53* | (2006.01) |
| *C07C 231/08* | (2006.01) |
| *C07C 281/02* | (2006.01) |
| *C07D 235/30* | (2006.01) |
| *C07D 239/95* | (2006.01) |
| *C07C 201/12* | (2006.01) |
| *C07C 231/14* | (2006.01) |
| *C07C 241/02* | (2006.01) |
| *C07D 233/88* | (2006.01) |

(52) U.S. Cl.
CPC .............. *C07C 253/30* (2013.01); *C07B 53/00* (2013.01); *C07B 2200/07* (2013.01); *C07C 67/343* (2013.01); *C07C 205/53* (2013.01); *C07C 231/08* (2013.01); *C07C 281/02* (2013.01); *C07C 2102/10* (2013.01); *C07D 235/30* (2013.01); *C07D 239/95* (2013.01); *C07C 201/12* (2013.01); *C07C 231/14* (2013.01); *C07C 241/02* (2013.01); *C07D 233/88* (2013.01)

(58) Field of Classification Search
CPC .............................. C07D 235/22; A01N 43/58
USPC ................................ 548/300.1, 307; 514/385
See application file for complete search history.

(56) References Cited

U.S. PATENT DOCUMENTS

| | | | |
|---|---|---|---|
| 6,797,706 B1 | 9/2004 | Hisamichi et al. | |
| 7,632,970 B2 | 12/2009 | Takemoto | |
| 7,655,817 B2 | 2/2010 | Takemoto et al. | |
| 2003/0199528 A1* | 10/2003 | Kanstrup et al. | ........... 514/263.2 |

FOREIGN PATENT DOCUMENTS

| | | |
|---|---|---|
| JP | 2006-240996 A | 9/2006 |
| WO | WO 00/76980 A1 | 12/2000 |
| WO | WO 01/00615 A1 | 1/2001 |
| WO | WO 2005/000803 A2 | 1/2005 |

OTHER PUBLICATIONS

Almasi et al., Journal of Organic Chemistry (2009), 74(16), 6163-6168.*
Almasi et al., *J. Org. Chemistry*, 74(16): 6163-6168 (2009).
Doyle et al., *Chem. Rev.*, 107: 5713-5743 (2007).
Feng et al., *J. Med. Chem.*, 50: 2297-2300 (2007).
Inokuma et al., *J. Am. Chem. Soc.*, 128: 9413-9419 (2006).
Kaik et al., *Tetrahedron: Asymmetry*, 14: 1559-1563 (2003).
Ognyanov et al., *J. Med. Chem.*, 49: 3719-3742 (2006).
Okino et al., *J. Am. Chem. Soc.*, 125: 12672-12673 (2003).
Ram et al., *Bioorganic & Medicinal Chemistry*, 11: 2439-2444 (2003).
Silvestri et al., *Bioorganic & Medicinal Chemistry*, 8: 2305-2309 (2000).
Terada et al., *J. Am. Chem. Soc.*, 128: 16044-16045 (2006).
Uyeda et al., *J. Am. Chem. Soc.*, 130: 9228-9229 (2008).
Xu et al., *Synlett*, 1: 137-140 (2005).
Zhang et al., *Advanced Synthesis & Catalysis.*, 351: 3063-3066 (2009).
European Patent Office, Extended European Search Report in European Patent Application No. 10761763.1 (Jun. 14, 2012).
Japanese Patent Office, International Search Report in International Patent Application No. PCT/JP2010/056463 (May 11, 2010) English translation.
Japanese Patent Office, International Preliminary Report on Patentability in International Patent Application No. PCT/JP2010/056463 (Nov. 15, 2011) English translation.

* cited by examiner

*Primary Examiner* — Paul V Ward
(74) *Attorney, Agent, or Firm* — Leydig, Voit & Mayer, Ltd.

(57) ABSTRACT

The invention provides a compound having a heterocyclic skeleton of formula (I):

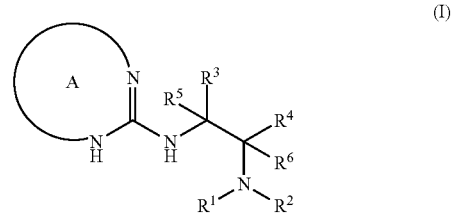

(I)

wherein the substituents are as defined in the specification, as well as a tautomer thereof or a salt thereof. The invention also provides asymmetric synthesis methods involving the use of such a compound, tautomer thereof, or salt thereof, as a catalyst.

11 Claims, No Drawings

COMPOUND HAVING HETERO RING SKELETON, AND PROCESS FOR PRODUCING OPTICALLY ACTIVE COMPOUND USING THE AFOREMENTIONED COMPOUND AS ASYMMETRIC CATALYST

CROSS-REFERENCE TO RELATED APPLICATIONS

This patent application is a divisional of U.S. patent application Ser. No. 13/259,887, filed Dec. 6, 2011, now U.S. Pat. No. 8,580,804, which is the U.S. national phase of International Patent Application No. PCT/JP2010/056463, filed Apr. 9, 2010, which claims the benefit of Japanese Patent Application No. 2009-096449, filed Apr. 10, 2009, all of which are incorporated by reference in their entireties herein.

TECHNICAL FIELD

The present invention relates to a novel compound having a heterocyclic skeleton which is useful as a catalyst for asymmetric synthesis. Moreover, the present invention relates to a production method of an optically active compound by an asymmetric conjugate addition reaction using the compound having a heterocyclic skeleton as a catalyst.

BACKGROUND ART

Optically active compounds obtained by asymmetric conjugate addition reaction to electron-deficient olefin such as nitroolefin compound, α,β-unsaturated carbonyl compound and the like are useful as intermediates for synthesizing amines, amino acids, medicaments, agricultural chemicals, food additives and the like (e.g., Journal of the American Chemical Society, vol. 124, No. 44, p. 13097-13105 (2002)), and various production methods have been reported so far.

In the reports, as a non-metal asymmetric catalyst for a conjugate addition reaction, it has been reported that asymmetric urea compound represented by the following formula:

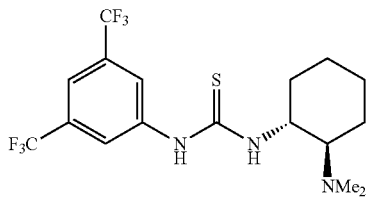 [SMILES: CN(C)[C@@H]1CCCC[C@H]1NC(=S)Nc1cc(C(F)(F)F)cc(C(F)(F)F)c1]

can be used as a non-metal asymmetric catalyst for a stereoselective conjugate addition reaction (patent document 1).

In addition, there are a number of biologically active compounds in the nature, such as lactacystin, myriocin, kaitocephalin, oxazolomycin and the like, which are expected to be applicable to pharmaceutical products. All of these compounds have an α-amino acid structure containing an optically active quaternary carbon, and are considered to be deeply involved in the biological activity. Construction of an asymmetric tetra-substituted carbon containing a nitrogen atom is an important object in the organic synthesis chemistry, and various synthesis methods have been reported heretofore.

Among them, a report has documented that the above-mentioned asymmetric urea compound can be used as a non-metal asymmetric catalyst for a stereoselective carbon-nitrogen bond formation reaction (patent document 2).

DOCUMENT LIST

Patent Document

Patent Document 1: WO 2005/000803
Patent Document 2: JP-A-2006-240996

SUMMARY OF THE INVENTION

Problems to be Solved by the Invention

However, the asymmetric urea disclosed in compound the above-mentioned patent document 1 or patent document 2 is useful as an asymmetric catalyst for a production of an optically active compound by a stereoselectivity asymmetric conjugate addition reaction or carbon-nitrogen bond formation reaction, the yield and/or optical purity of the obtained optically active compound have room for improvement. The aim of the present invention is to provide a compound having a heterocyclic skeleton, a tautomer thereof or a salt thereof (hereinafter these are sometimes to be generically referred to as "the compound of the present invention") which is useful as a non-metal asymmetric catalyst capable of achieving an asymmetric conjugate addition reaction or carbon-nitrogen bond formation reaction in a high yield and with high stereoselectivity, and to provide an asymmetric conjugate addition reaction or carbon-nitrogen bond formation reaction using the asymmetric catalyst. The asymmetric catalyst provided according to the present invention can provide an advantageous production method of an optically active compound.

Means of Solving the Problems

The present inventors took note of a compound wherein both of an acidic moiety that activates an electron-deficient olefin and a basic moiety that activates a nucleophilic reagent are bonded to optically active scaffolds, as a non-metallic asymmetric catalyst for a conjugate addition reaction, and conducted intensive studies. Consequently, they found a novel compound having a heterocyclic skeleton, which resulted in the completion of the present invention.

In addition, the present inventors took note of a compound wherein both of an acidic moiety that activates an azo compound and a basic moiety that activates a carbon atom having an activated hydrogen are bonded to optically active scaffolds, as a non-metallic asymmetric catalyst, and conducted intensive studies. Consequently, they found a novel compound having a heterocyclic skeleton, which resulted in the completion of the present invention.

Accordingly, the present invention is as described below.

[1] A compound having a heterocyclic skeleton, which is represented by of the formula (I):

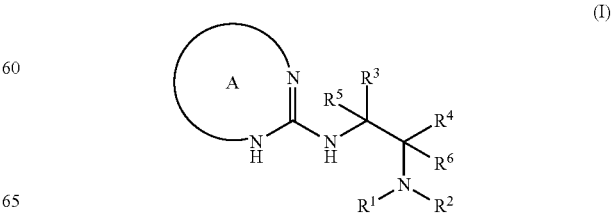

wherein
$R^1$ and $R^2$ are the same or different and each is a lower alkyl group optionally having substituent(s), an aralkyl group optionally having substituent(s) or an aryl group optionally having substituent(s), or
$R^1$ and $R^2$ in combination form, together with the nitrogen atom they are bonded to, a heterocycle optionally having substituent(s) (the heterocycle is optionally condensed with an aromatic hydrocarbon ring);
ring A is an imidazole ring condensed with an aromatic ring optionally having substituent(s), or a pyrimidin-4-one ring condensed with an aromatic ring optionally having substituent(s);
$R^3$ and $R^4$ are the same or different and each is a lower alkyl group optionally having substituent(s), a lower alkenyl group optionally having substituent(s), a lower alkynyl group optionally having substituent(s), an aralkyl group optionally having substituent(s) or an aryl group optionally having substituent(s), or
$R^3$ and $R^4$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring); and
$R^5$ and $R^6$ are the same or different and each is a hydrogen atom or a lower alkyl group optionally having substituent(s), a tautomer thereof or a salt thereof (hereinafter referred to as compound (I)).

[2] A compound having a heterocyclic skeleton, which is represented by the formula (II):

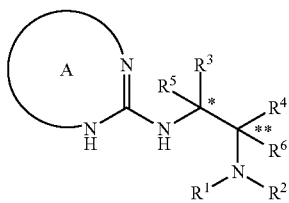

wherein
$R^1$ and $R^2$ are the same or different and each is a lower alkyl group optionally having substituent(s), an aralkyl group optionally having substituent(s) or an aryl group optionally having substituent(s), or
$R^1$ and $R^2$ in combination form, together with the nitrogen atom they are bonded to, a heterocycle optionally having substituent(s) (the heterocycle is optionally condensed with an aromatic hydrocarbon ring);
ring A is an imidazole ring condensed with an aromatic ring optionally having substituent(s), or a pyrimidin-4-one ring condensed with an aromatic ring optionally having substituent(s);
$R^3$ and $R^4$ are the same or different and each is a lower alkyl group optionally having substituent(s), a lower alkenyl group optionally having substituent(s), a lower alkynyl group optionally having substituent(s), an aralkyl group optionally having substituent(s) or an aryl group optionally having substituent(s), or
$R^3$ and $R^4$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring);

$R^5$ and $R^6$ are the same or different and each is a hydrogen atom or a lower alkyl group optionally having substituent(s); and
C* and C** are each an asymmetric carbon,
a tautomer thereof or a salt thereof (hereinafter referred to as compound (II)).

[3] The compound of the above-mentioned [1] or [2], wherein $R^1$ and $R^2$ are the same or different and each is a lower alkyl group optionally having substituent(s), a tautomer thereof or a salt thereof.

[4] The compound of any of the above-mentioned [1] to [3], wherein $R^3$ and $R^4$ in combination form, together with the carbon atoms they are respectively bonded to, a cycloalkane having 3 to 6 carbon atoms and optionally having substituent(s), a tautomer thereof or a salt thereof.

[5] The compound of any of the above-mentioned [1] to [4], wherein $R^5$ and $R^6$ are both hydrogen atoms, a tautomer thereof or a salt thereof.

[6] The compound of any of the above-mentioned [2] to [5], wherein C* and C** are both R-configurations or both S-configurations, a tautomer thereof or a salt thereof.

[7] A compound having a quinazolin-4-one skeleton, which is represented by the formula (III):

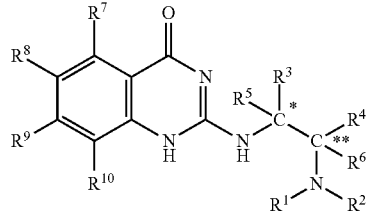

wherein
$R^1$ and $R^2$ are the same or different and each is a lower alkyl group optionally having substituent(s), an aralkyl group optionally having substituent(s) or an aryl group optionally having substituent(s), or
$R^1$ and $R^2$ in combination form, together with the nitrogen atom they are bonded to, a heterocycle optionally having substituent(s) (the heterocycle is optionally condensed with an aromatic hydrocarbon ring);
$R^3$ and $R^4$ are the same or different and each is a lower alkyl group optionally having substituent(s), a lower alkenyl group optionally having substituent(s), a lower alkynyl group optionally having substituent(s), an aralkyl group optionally having substituent(s) or an aryl group optionally having substituent(s), or
$R^3$ and $R^4$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring);
$R^5$ and $R^6$ are the same or different and each is a hydrogen atom or a lower alkyl group optionally having substituent(s);
$R^7$, $R^8$, $R^9$ and $R^{10}$ are the same or different and each is a hydrogen atom, a halogen atom, a hydroxyl group, a lower alkyl group optionally having substituent(s), an aralkyl group optionally having substituent(s), an aryl group optionally having substituent(s) or a lower alkoxy group optionally having substituent(s); and
C* and C** are each an asymmetric carbon,
a tautomer thereof or a salt thereof (hereinafter referred to as compound (III)).

[8] An optically active compound having a quinazolin-4-one skeleton, which is represented by the following formula:

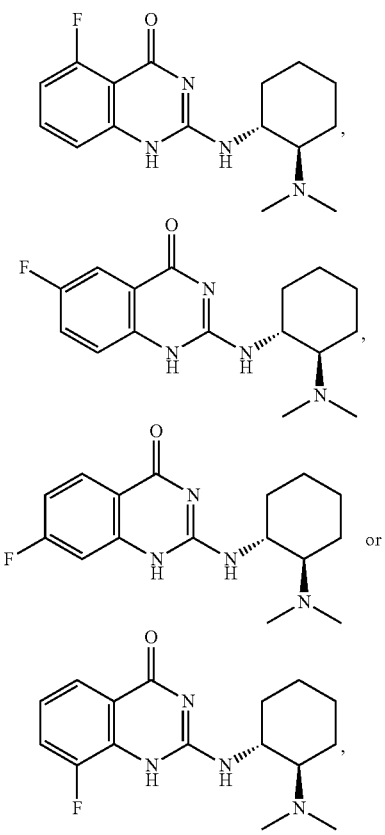

a tautomer thereof or a salt thereof.
[9] A compound having a benzimidazole skeleton, which is represented by the formula (IV)

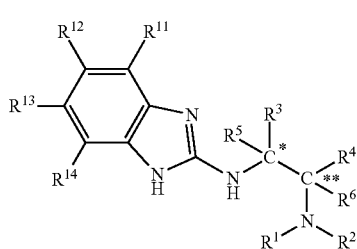

(IV)

wherein
$R^1$ and $R^2$ are the same or different and each is a lower alkyl group optionally having substituent(s), an aralkyl group optionally having substituent(s) or an aryl group optionally having substituent(s), or
$R^1$ and $R^2$ in combination form, together with the nitrogen atom they are bonded to, a heterocycle optionally having substituent(s) (the heterocycle is optionally condensed with an aromatic hydrocarbon ring);
$R^3$ and $R^4$ are the same or different and each is a lower alkyl group optionally having substituent(s), a lower alkenyl group optionally having substituent(s), a lower alkynyl group optionally having substituent(s), an aralkyl group optionally having substituent(s) or an aryl group optionally having substituent(s), or $R^3$ and $R^4$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring);
$R^5$ and $R^6$ are the same or different and each is a hydrogen atom or a lower alkyl group optionally having substituent(s);
$R^{11}$, $R^{12}$, $R^{13}$ and $R^{14}$ are the same or different and each is a hydrogen atom, a halogen atom, a hydroxyl group, a lower alkyl group optionally having substituent(s), an aralkyl group optionally having substituent(s), an aryl group optionally having substituent(s) or a lower alkoxy group optionally having substituent(s); and
C* and C** are each an asymmetric carbon,
or a salt thereof (hereinafter referred to as compound (IV)).
[10] An optically active compound having a benzimidazole skeleton, which is represented by the following formula:

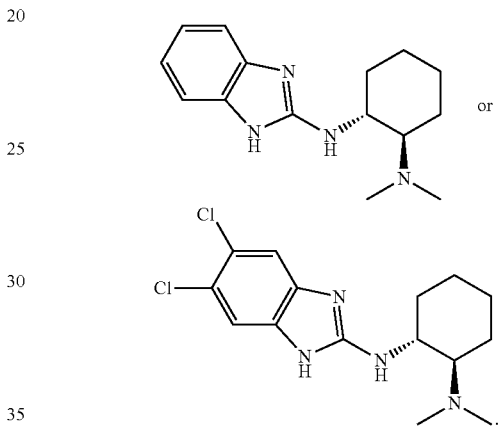

or a salt thereof.
[11] A method of producing a compound represented by the formula (VII):

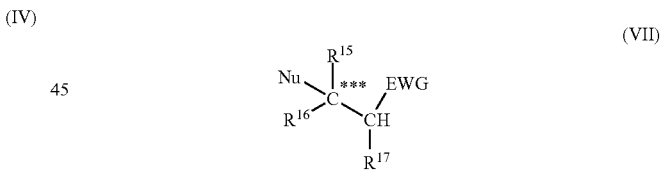

(VII)

wherein
$R^{15}$, $R^{16}$ and $R^{17}$ are the same or different and each is a hydrogen atom, a lower alkyl group optionally having substituent(s), an aralkyl group optionally having substituent(s), an aryl group optionally having substituent(s), a heteroaryl group optionally having substituent(s), a hetero atom optionally having substituent(s), and an electron withdrawing group, or
$R^{16}$ and $R^{17}$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring), provided that $R^{15}$ and $R^{16}$ are not the same groups;
EWG is an electron withdrawing group selected from a nitro group, a cyano group, —$COR^{18}$, —$SO_2R^{19}$, —$COOR^{20}$, —$CONHCOR^{21}$ and —$PO(OR^{22})(OR^{23})$ wherein $R^{18}$, $R^{19}$, $R^{20}$, $R^{21}$, $R^{22}$ and $R^{23}$ are the same or different and each is a hydrogen atom, a lower alkyl group optionally having substituent(s), an aralkyl group optionally having substituent(s), an aryl group optionally having substituent(s) or a heteroaryl group optionally having substituent(s), or $R^{18}$ and $R^{15}$ or $R^{18}$ and $R^{17}$ in combination form, together with the carbon atoms they are respectively bonded to, a homocycle having an electron withdrawing group and optionally having substituent(s) (the homocycle is optionally condensed with an aromatic hydrocarbon ring);

Nu is $-CR^{24}(COR^{25})(COR^{26})$, $-CR^{27}(CN)_2$, $-OR^{28}$, $-SR^{29}$, $-NR^{30}R^{31}$ or $-C(NO_2)R^{32}R^{33}$ wherein $R^{24}$ is a hydrogen atom, a halogen atom, a hetero atom having substituent(s), a lower alkyl group optionally having substituent(s) or an aryl group optionally having substituent(s);

$R^{25}$ and $R^{26}$ are the same or different and each is a hydrogen atom, a lower alkyl group, a lower alkoxy group, a mono-lower alkylamino group or a di-lower alkylamino group, or;

$R^{24}$ and $R^{25}$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring);

$R^{27}$ is a hydrogen atom, a halogen atom, a hetero atom having substituent(s), a lower alkyl group optionally having substituent(s) or an aryl group optionally having substituent(s);

$R^{28}$, $R^{29}$, $R^{30}$, $R^{31}$, $R^{32}$ and $R^{33}$ are the same or different and each is a hydrogen atom, a lower alkyl group optionally having substituent(s), an aralkyl group optionally having substituent(s), an aryl group optionally having substituent(s) or a heteroaryl group optionally having substituent(s), or $R^{30}$ and $R^{31}$ in combination form, together with the nitrogen atom they are bonded to, a heterocycle optionally having substituent(s) (the heterocycle is optionally condensed with an aromatic hydrocarbon ring), or an azido group; and C*** is an asymmetric carbon, or a salt thereof (hereinafter referred to as compound (VII)), which comprises conjugately adding a nucleophilic reagent represented by the formula (VI): H-Nu (VI) wherein Nu is as defined above (hereinafter referred to as compound (VI)), to a compound represented by the formula (V):

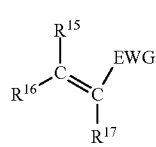

(V)

wherein each symbol is as defined above, or a salt thereof (hereinafter referred to as compound (V)), in the presence of the compound of any of the above-mentioned [1] to [10], a tautomer thereof or a salt thereof.

[12] A method of producing a compound represented by the formula (X):

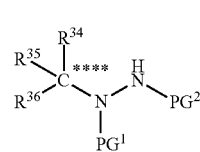

(X)

wherein $PG^1$ and $PG^2$ are the same or different and each is a protecting group, $R^{34}$ is a hydrogen atom, a lower alkyl group optionally having substituent(s), an aralkyl group optionally having substituent (s), an aryl group optionally having substituent(s) or a heteroaryl group optionally having substituent(s);

$R^{35}$ and $R^{36}$ are the same or different and each is an electron withdrawing group, provided that $R^{35}$ and $R^{36}$ are not the same groups; or $R^{34}$ and $R^{35}$ in combination form, together with the carbon atom they are bonded to, a ring having an electron withdrawing group and optionally having substituent(s) (the ring is optionally condensed with an aromatic hydrocarbon ring); and C*** is an asymmetric carbon, or a salt thereof (hereinafter referred to as compound (X)), which comprises adding a compound represented by the formula (IX):

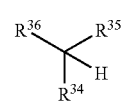

(IX)

wherein each symbol is as defined above (hereinafter referred to as compound (IX)), to a compound represented by the formula (VIII):

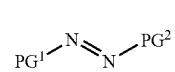

(VIII)

wherein each symbol is as defined above (hereinafter referred to as compound (VIII)), in the presence of the compound of any of the above-mentioned [1] to [10], a tautomer thereof or a salt thereof.

[13] The method of the above-mentioned [12], wherein $PG^1$ and $PG^2$ are the same or different and each is $-CO_2R^{37}$ or $-CONR^{38}R^{39}$ wherein $R^{37}$, $R^{38}$ and $R^{39}$ are the same or different and each is a lower alkyl group optionally having substituent(s), an aralkyl group optionally having substituent(s), an aryl group optionally having substituent(s) or a heteroaryl group optionally having substituent(s), or $R^{38}$ and $R^{39}$ in combination form, together with the nitrogen atom they are bonded to, a heterocycle optionally having substituent(s) (the heterocycle is optionally condensed with an aromatic hydrocarbon ring).

[14] The method of the above-mentioned [12] or [13], wherein $R^{35}$ and $R^{36}$ are the same or different and each is a cyano group, a nitro group, $-P(=O)R^{40}R^{41}$, $-SO_2R^{42}$, $CO_2R^{43}$, $-CONR^{44}R^{45}$ or $-COR^{46}$ wherein R$^{40}$, R$^{41}$, R$^{42}$, R$^{43}$, R$^{44}$, R$^{45}$ and R$^{46}$ are the same or different and each is a hydrogen atom, a lower alkyl group optionally having substituent(s), an aralkyl group optionally having substituent(s), an aryl group optionally having substituent(s) or a heteroaryl group optionally having substituent(s), or R$^{44}$ and R$^{45}$ in combination form, together with the nitrogen atom they are bonded to, a heterocycle optionally having substituent(s) (the heterocycle is optionally condensed with an aromatic hydrocarbon ring).

[15] The method of any of the above-mentioned [12] to [14], wherein the ring having an electron withdrawing group and optionally having substituent(s) which is formed by R$^{34}$ and R$^{35}$ is cyclopentanone, cyclohexanone, 1-indanone or 1,2,3,4-tetrahydro-1-oxonaphthalene, each of which optionally has substituent(s).

Effect of the Invention

According to the present invention, compound (VII) can be produced in a high yield and with high stereoselectivity by conjugately adding nucleophilic reagent (VI) to compound (V) using compound (II) as an asymmetric catalyst.

In addition, compound (X) can be produced in a high yield and with high stereoselectivity by adding compound (IX) to compound (VIII) using compound (II) as an asymmetric catalyst. The obtained compound (X) can be easily converted into the below-mentioned compound (XV) by the cleavage of the nitrogen-nitrogen bond.

In addition, since compound (II) is non-metallic, it does not require treatments of metal waste liquid and the like, and therefore, it is an environmentally-friendly catalyst. Moreover, since it is non-metallic, the compound can be recovered and reused easily.

MODE FOR CARRYING OUT THE INVENTION

The present invention is described in detail in the following.

First, each symbol used in the present description is defined in the following.

The alkyl used in the present invention is linear when it is free of a prefix (e.g., iso, neo, sec-, tert- and the like). For example, a simple propyl means linear propyl.

Examples of the "halogen atom" for R$^7$ to R$^{14}$, R$^{24}$ or R$^{27}$ include a fluorine atom, a chlorine atom, a bromine atom and an iodine atom. Preferred are a fluorine atom, a chlorine atom and a bromine atom.

Examples of the "lower alkyl group" for R$^{25}$ or R$^{26}$ include a straight chain or branched chain alkyl group having 1 to 12 carbon atoms, and specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl and the like. Preferred is a straight chain or branched chain alkyl group having 1 to 6 carbon atoms, and more preferred are methyl, ethyl and propyl.

Examples of the "lower alkoxy group" for R$^{25}$ or R$^{26}$ include an alkoxy group wherein the alkyl moiety is the "lower alkyl group" defined above, and specific examples thereof include methoxy, ethoxy, propoxy, isopropoxy, butoxy, isobutoxy, sec-butoxy, tert-butoxy, pentoxy, isopentoxy, neopentoxy, hexyloxy, heptyloxy, octyloxy, nonyloxy, decyloxy, undecyloxy, dodecyloxy and the like. Preferred is a straight chain or branched chain alkoxy group having 1 to 6 carbon atoms, and more preferred are methoxy and ethoxy.

Examples of the "mono-lower alkylamino group" for R$^{25}$ or R$^{26}$ include a mono-alkylamino group wherein the alkyl moiety is the "lower alkyl group" defined above, and specific examples thereof include N-methylamino, N-ethylamino, N-propylamino, N-isopropylamino, N-butylamino, N-isobutylamino, N-sec-butylamino, N-tert-butylamino, N-pentylamino, N-isopentylamino, N-neopentylamino, N-hexylamino, N-heptylamino, N-octylamino, N-nonylamino, N-decylamino, N-undecylamino, N-dodecylamino and the like.

Examples of the "di-lower alkylamino group" for R$^{25}$ or R$^{26}$ include a di-alkylamino group wherein the alkyl moieties are the same or different and each is the "lower alkyl group" defined above, and specific examples thereof include N,N-dimethylamino, N,N-diethylamino, N,N-dipropylamino, N,N-diisopropylamino, N,N-dibutylamino, N,N-diisobutylamino, N,N-di-sec-butylamino, N,N-di-tert-butylamino, N,N-dipentylamino, N,N-diisopentylamino, N,N-dineopentylamino, N,N-dihexylamino, N,N-diheptylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-tert-butylamino, N-methyl-N-pentylamino, N-methyl-N-isopentylamino, N-methyl-N-neopentylamino, N-methyl-N-hexylamino, N-methyl-N-heptylamino, N-methyl-N-octylamino, N-methyl-N-nonylamino, N-methyl-N-decylamino, N-methyl-N-undecylamino, N-methyl-N-dodecylamino and the like.

Examples of the "lower alkyl group" of the "lower alkyl group optionally having substituent(s)" for R$^1$ to R$^{24}$, R$^{27}$ to R$^{34}$ or R$^{37}$ to R$^{46}$ include those same as the "lower alkyl group" defined above.

The lower alkyl group optionally has substituent(s) at substitutable position(s), and examples of the substituent(s) include a lower alkoxy group (exemplified by those defined above), a mono-lower alkylamino group (exemplified by those defined above), a di-lower alkylamino group (exemplified by those defined above), a halogen atom (exemplified by those defined above), a nitro group, a cyano group, —COOR$^{51}$ wherein R$^{51}$ is a lower alkyl group same as those defined above, and the like. When it has substituent(s), the number of substituents is not particularly limited, but is preferably 1 to 3. When it is 2 or more, the substituents may be the same or different.

Examples of the "lower alkenyl group" of the "lower alkenyl group optionally having substituent(s)" for R$^3$ or R$^4$ include a straight chain or branched chain alkenyl group having 2 to 12 carbon atoms, and specific examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like. Preferred is a straight chain or branched chain alkenyl group having 2 to 6 carbon atoms.

The lower alkenyl group optionally has substituent(s) at substitutable position(s), and examples of the substituent(s) include substituents same as those exemplified for the "lower alkyl group optionally having substituent(s)" mentioned above. When it has substituent(s), the number of substituents is not particularly limited, but is preferably 1 to 3. When it is 2 or more, the substituents may be the same or different.

Examples of the "lower alkynyl group" of the "lower alkynyl group optionally having substituent(s)" for R$^3$ or R$^4$ include a straight chain or branched chain alkynyl group having 2 to 12 carbon atoms, and specific examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Preferred is a straight chain or branched chain alkynyl group having 2 to 6 carbon atoms.

The lower alkynyl group optionally has substituent(s) at substitutable position(s), and examples of the substituent(s) include substituents same as those exemplified for the "lower alkyl group optionally having substituent(s)" mentioned above. When it has substituent(s), the number of substituents is not particularly limited, but is preferably 1 to 3. When it is 2 or more, the substituents may be the same or different.

Examples of the "lower alkoxy group" of the "lower alkoxy group optionally having substituent(s)" for $R^7$ to $R^{14}$ include those same as the "lower alkoxy group" defined above.

The lower alkoxy group optionally has substituent(s) at substitutable position(s), and examples of the substituent(s) include substituents same as those exemplified for the "lower alkyl group optionally having substituent(s)" mentioned above. When it has substituent(s), the number of substituents is not particularly limited, but is preferably 1 to 3. When it is 2 or more, the substituents may be the same or different.

Examples of the "aryl group" of the "aryl group optionally having substituent(s)" for $R^1$ to $R^4$, $R^7$ to $R^{24}$, $R^{27}$ to $R^{34}$, or $R^{37}$ to $R^{46}$ include an aryl group having 6 to 20 carbon atoms, and specific examples thereof include phenyl, 1- or 2-naphthyl, biphenylyl, binaphthylyl and the like. Preferred is an aryl group having 6 to 10 carbon atoms.

The aryl group has substituent(s) at substitutable position(s), and examples of the substituent(s) include a lower alkyl group (exemplified by those defined above), a lower alkoxy group (exemplified by those defined above), a mono-lower alkylamino group (exemplified by those defined above), a di-lower alkylamino group (exemplified by those defined above), a halogen atom (exemplified by those defined above), a haloalkyl group (i.e. a lower alkyl group (exemplified by those defined above) substituted by one or more halogen atoms, for example, trifluoromethyl etc.), a nitro group, a cyano group, —COOR$^{51}$ wherein R$^{51}$ is as defined above) and the like. When it has substituent(s), the number of substituents is not particularly limited, but is preferably 1 to 3. When it is 2 or more, the substituents may be the same or different.

Examples of the "aralkyl group" of the "aralkyl group optionally having substituent(s)" for $R^1$ to $R^4$, $R^7$ to $R^{23}$, $R^{28}$ to $R^{34}$, or $R^{37}$ to $R^{46}$ include an aralkyl group wherein the "lower alkyl group" defined above is substituted by the "aryl group" defined above at optional position(s), and specific examples thereof include benzyl, 1- or 2-phenethyl, 1-, 2- or 3-phenylpropyl, 1- or 2-naphthylmethyl, benzhydryl, trityl and the like.

The aralkyl group has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "heteroaryl group" of the "heteroaryl group optionally having substituent(s)" for $R^{15}$ to $R^{23}$, $R^{28}$ to $R^{34}$, $R^{37}$ to $R^{46}$ include a 5- to 10-membered aromatic heterocyclic group containing, besides carbon atoms, 1 to 3 hetero atoms selected from an oxygen atom, a sulfur atom and a nitrogen atom, a fused heterocyclic group thereof and the like. Specific examples thereof include 2- or 3-thienyl, 2- or 3-furyl, 1-, 2- or 3-pyrrolyl, 1-, 2-, 4- or 5-imidazolyl, 2-, 4- or 5-oxazolyl, 2-, 4- or 5-thiazolyl, 1-, 3-, 4- or 5-pyrazolyl, 3-, 4- or 5-isoxazolyl, 3-, 4- or 5-isothiazolyl, 1,2,4-triazol-1-, 3-, 4- or 5-yl, 1,2,3-triazol-1-, 2- or 4-yl, 1H-tetrazol-1- or 5-yl, 2H-tetrazol-2- or 5-yl, 2-, 3- or 4-pyridyl, 2-, 4- or 5-pyrimidinyl, 1-, 2-, 3-, 4-, 5-, 6- or 7-indolyl, 2-, 3-, 4-, 5-, 6- or 7-benzofuryl, 2-, 3-, 4-, 5-, 6- or 7-benzothienyl, 1-, 2-, 4-, 5-, 6- or 7-benzimidazolyl, 2-, 3-, 4-, 5-, 6-, 7- or 8-quinolyl, 1-, 3-, 4-, 5-, 6-, 7- or 8-isoquinolyl and the like.

The heteroaryl group has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "hetero atom" of the "hetero atom optionally having substituent(s)" for $R^{15}$ to $R^{17}$ include a nitrogen atom, an oxygen atom, a sulfur atom and the like.

Examples of the substituent that the hetero atom optionally has include a "lower alkyl group optionally having substituent(s)", an "aralkyl group optionally having substituent(s)", an "aryl group optionally having substituent(s)", a "heteroaryl group optionally having substituent(s)" and the like, each of which is defined above.

Examples of the "hetero atom" of the "hetero atom having substituent(s)" for $R^{24}$ or $R^{27}$ include a nitrogen atom, an oxygen atom, a sulfur atom and the like.

Examples of the substituent that the hetero atom has include a "lower alkyl group optionally having substituent(s)", an "aralkyl group optionally having substituent(s)", an "aryl group optionally having substituent(s)" and a "heteroaryl group optionally having substituent(s)", each of which is defined above, and —COOR$^{52}$, —COR$^{53}$ and —SO$_2$R$^{54}$ wherein R$^{52}$, R$^{53}$ and R$^{54}$ are the same or different and each is an alkyl group same as those defined above, and the like.

Examples of the "aromatic ring" of the "imidazole ring condensed with an aromatic ring optionally having substituent(s)" for ring A, and the "aromatic ring" of the "pyrimidin-4-one ring condensed with an aromatic ring optionally having substituent(s)" for ring A include an aromatic hydrocarbon ring and an aromatic heterocycle.

Examples of the aromatic hydrocarbon ring include an aromatic hydrocarbon ring having 6 to 20 carbon atoms, and specific examples thereof include benzene, 1- or 2-naphthalene, biphenyl, binaphthyl and the like. Preferred is an aromatic hydrocarbon ring having 6 to 10 carbon atoms.

Examples of the aromatic heterocycle include thiophene, furan, pyrrole, imidazole, oxazole, thiazole, pyrazole, isoxazole, isothiazole, 1,2,4-triazole, 1,2,3-triazole, 1H-tetrazole, 2H-tetrazole, pyridine, pyrimidine, indole, benzofuran, benzothiophene, benzimidazole, quinoline, isoquinoline and the like.

The aromatic ring has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "heterocycle" of the "heterocycle optionally having substituent(s)" formed by $R^1$ and $R^2$ in combination, $R^{30}$ and $R^{31}$ in combination, $R^{38}$ and $R^{39}$ in combination, or $R^{44}$ and $R^{45}$ in combination together with the nitrogen atom they are bonded to include a 5- to 10-membered aliphatic heterocycle containing carbon atom(s) and at least one nitrogen atom and, besides these, optionally containing 1 to 3 hetero atoms selected from an oxygen atom, a sulfur atom and a nitrogen atom. Specific examples thereof include pyrrolidine, piperidine, morpholine, thiomorpholine, piperazine and the like.

The heterocycle is optionally condensed with an aromatic hydrocarbon ring, and examples of the aromatic hydrocarbon ring include benzene, naphthalene, biphenyl, binaphthyl and the like.

The heterocycle has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "heterocycle" of the "heterocycle optionally having substituent(s)" formed by $R^3$ and $R^4$ in combination together with the carbon atoms they are respectively bonded to include a 5- to 10-membered aliphatic heterocycle containing carbon atom(s) and at least one nitrogen atom and, besides these, optionally containing 1 to 3 hetero atoms selected from an oxygen atom, a sulfur atom and a nitrogen atom. Specific examples thereof include pyrrolidine, piperidine, morpholine, thiomorpholine, piperazine and the like.

The heterocycle is optionally condensed with an aromatic hydrocarbon ring, and examples of the aromatic hydrocarbon ring include benzene, naphthalene, biphenyl, binaphthyl and the like.

The heterocycle has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "heterocycle" of the "heterocycle optionally having substituent(s)" formed by $R^{16}$ and $R^{17}$ in combination together with the carbon atoms they are respectively bonded to include a 5- to 10-membered heterocycle having the double bond of compound (V) and containing, beside carbon atoms, 1 to 3 hetero atoms selected from an oxygen atom, a sulfur atom and a nitrogen atom. Specific examples thereof include 5,6-dihydro-2H-pyran, 3,4-dihydro-2H-pyran, 2,3- or 2,5-dihydrofuran, 2- or 3-pyrroline, 1,2,3,4- or 1,2,3,6-tetrahydropyridine and the like.

The heterocycle is optionally condensed with an aromatic hydrocarbon ring, and examples of the aromatic hydrocarbon ring include benzene, naphthalene, biphenyl, binaphthyl and the like.

The heterocycle has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "heterocycle" of the "heterocycle optionally having substituent(s)" formed by $R^{24}$ and $R^{25}$ in combination together with the carbon atoms they are respectively bonded to include a 5- to 10-membered heterocycle substituted by oxo and containing, beside carbon atoms, 1 to 3 hetero atoms selected from an oxygen atom, a sulfur atom and a nitrogen atom. Specific examples thereof include tetrahydropyranone, tetrahydrofuranone, pyrrolidone, piperidone and the like.

The heterocycle is optionally condensed with an aromatic hydrocarbon ring, and examples of the aromatic hydrocarbon ring include benzene, naphthalene, biphenyl, binaphthyl and the like.

The heterocycle has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "homocycle" of the "homocycle optionally having substituent(s)" formed by $R^3$ and $R^4$ in combination together with the carbon atoms they are respectively bonded to include a cycloalkane having 3 to 7 carbon atoms (e.g., cyclopropane, cyclobutane, cyclopentane, cyclohexane, cycloheptane etc.), a cycloalkene having 4 to 7 carbon atoms (e.g., cyclobutene, cyclopentene, cyclohexene, cycloheptene etc.) and the like. Preferred are a cycloalkane having 3 to 6 carbon atoms (e.g., cyclopropane, cyclobutane, cyclopentane, cyclohexane etc.) and the like, and more preferred are cyclohexane and the like.

The homocycle is optionally condensed with an aromatic hydrocarbon ring, and examples of the aromatic hydrocarbon ring include benzene, naphthalene, biphenyl, binaphthyl and the like.

The homocycle has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "homocycle" of the "homocycle optionally having substituent(s)" formed by $R^{16}$ and $R^{17}$ in combination together with the carbon atoms they are respectively bonded to include a cycloalkene having 3 to 7 carbon atoms (e.g., cyclobutene, cyclopentene, cyclohexene, cycloheptene etc.) having the double bond of compound (V), and the like.

The homocycle is optionally condensed with an aromatic hydrocarbon ring, and examples of the aromatic hydrocarbon ring include benzene, naphthalene, biphenyl, binaphthyl and the like.

The homocycle has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

Examples of the "homocycle" of the "homocycle optionally having substituent(s)" formed by $R^{24}$ and $R^{25}$ in combination together with the carbon atoms they are respectively bonded to include a cycloalkanone having 3 to 7 carbon atoms (e.g., cyclobutanone, cyclopentanone, cyclohexanone, cycloheptanone etc.) and a cycloalkenone having 3 to 7 carbon atoms (e.g., cyclopentenone, cyclohexenone, cycloheptenone etc.), each of which is substituted by oxo, and the like. Preferred are cyclobutanone, cyclopentanone, cyclohexanone and the like, and more preferred are cyclohexanone and the like.

The homocycle is optionally condensed with an aromatic hydrocarbon ring, and examples of the aromatic hydrocarbon ring include benzene, naphthalene, biphenyl, binaphthyl and the like.

The homocycle has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

The "electron withdrawing group" for $R^{15}$ to $R^{17}$ or EWG is not particularly limited as long as it sufficiently absorbs the electron of the double bond of compound (V), so that the conjugate addition of nucleophilic reagent (VI) to the double bond can be afforded. Examples thereof include a nitro group, a cyano group, $-COR^{18}$, $-SO_2R^{19}$, $-COOR^{20}$ and $-CONHCOR^{21}$, $-PO(OR^{22})(OR^{23})$ wherein each symbol is as defined above, and the like. Preferred are a nitro group, $-CONHCOR^{21}$ and the like. $R^{15}$, $R^{16}$, $R^{17}$ and EWG may be the same or different, however, $R^{15}$ and $R^{16}$ are not the same groups.

When the "electron withdrawing group" for EWG is $-COR^{18}$ wherein each symbol is as defined above, $R^{18}$ and $R^{15}$ in combination or $R^{18}$ and $R^{17}$ in combination optionally form, together with the carbon atoms they are respectively bonded to, a "homocycle having an electron withdrawing group and optionally having substituent(s)".

Examples of the "homocycle having an electron withdrawing group" of the "homocycle having an electron withdrawing group and optionally having substituent(s)" formed by $R^{18}$ and $R^{15}$ in combination together with the carbon atoms they are respectively bonded to include a cycloalkenone having 4 to 7 carbon atoms (e.g., 2-cyclopenten-1-one, 2-cyclohexen-1-one, 2-cyclohepten-1-one etc.) and having the double bond of compound (V) and carbonyl as a an electron withdrawing group.

Examples of the "homocycle having an electron withdrawing group" of the "homocycle having an electron withdrawing group and optionally having substituent(s)" formed by $R^{18}$ and $R^{17}$ in combination together with the carbon atoms they are respectively bonded to include a cycloalkanone having 4 to 7 carbon atoms (e.g., cyclobutanone, 2-cyclopentanone, cyclohexanone, cycloheptanone etc.) having carbonyl as a an electron withdrawing group.

The "homocycle having an electron withdrawing group" is optionally condensed with aromatic hydrocarbon ring (e.g., benzene, naphthalene, biphenyl, binaphthyl etc.).

The "homocycle having an electron withdrawing group" has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

The "electron withdrawing group" for $R^{35}$ or $R^{36}$ is not particularly limited as long as the adjacent carbon atom is acidified so that it can be anionized by the basic moiety (amino group) of compound (II). Examples of the electron withdrawing group include a cyano group, a nitro group, $-P(=O)R^{40}R^{41}$, $-SO_2R^{42}$, $-CO_2R^{43}$, $-CONR^{44}R^{45}$ and $-COR^{46}$ wherein each symbol is as defined above, and the like. Preferred are a cyano group, $-CO_2R^{43}$, $-CONR^{44}R^{45}$, $-COR^{46}$ and the like, and particularly preferred are $-CO_2R^{43}$ and the like, however, $R^{35}$ and $R^{36}$ are not the same groups.

The "ring having an electron withdrawing group" of the "ring having an electron withdrawing group and optionally having substituent(s)" formed by $R^{34}$ and $R^{35}$ in combination together with the carbon atom they are bonded to is not particularly limited as long as the electron withdrawing group has the above-mentioned properties. Examples thereof include a cycloalkanone having a carbon number of 3 to 7 (e.g., cyclopentanone, cyclohexanone, cycloheptane etc.), a lactone having 3 to 5 carbon atoms (e.g., γ-butyrolactone, δ-valerolactone etc.), a lactam having 3 to 5 carbon atoms (e.g., γ-butyrolactam, δ-valerolactam etc.) and the like. Preferred are cyclopentanone, cyclohexanone and the like.

The "ring having an electron withdrawing group" is optionally condensed with an aromatic hydrocarbon ring, and examples of the aromatic hydrocarbon ring include benzene, naphthalene, biphenyl, binaphthyl and the like.

The "ring having an electron withdrawing group" has substituent(s) at substitutable position(s), and examples of the substituent(s) include substituents same as those exemplified for the "aryl group optionally having substituent(s)" mentioned above. When it has substituent(s), the number of substituents is not particularly limited, but is preferably 1 to 3. When it is 2 or more, the substituents may be the same or different.

The "protecting group" for $PG^1$ or $PG^2$ is not particularly limited as long as it is a protecting group known per se used as an amino-protecting group, it is preferably an electron-withdrawing protecting group from the aspect of the stabilization of the azo group of compound (VIII). Examples of the protecting group include $-CO_2R^{37}$ and $-CONR^{38}R^{39}$ wherein each symbol is as defined above, and the like. Preferred are ethoxycarbonyl, isopropoxycarbonyl, benzyloxycarbonyl, tert-butoxycarbonyl and the like, and particularly preferred are tert-butoxycarbonyl and the like. $PG^1$ and $PG^2$ may be the same or different.

The "asymmetric carbon" for C*, C, C* or C**** has an independent absolute configuration, and is not particularly limited. The absolute configurations of C* and C** in compound (II) can be appropriately selected to obtain compound (VII) or (X) having a desired configuration.

Compounds (I) to (V), (VII) and (X) may be in the form of a salt. Examples of the salt include salts with inorganic acid (e.g., hydrochloride, sulfate, nitrate, phosphate etc.); salts with organic acid (e.g., acetate, propionate, methanesulfonate, 4-toluenesulfonate, oxalate, maleate etc.); alkali metal salts (e.g., sodium salt, potassium salt etc.); alkaline earth metal salts (e.g., calcium salt, magnesium salt etc.); salts with organic base (e.g., trimethylamine salt, triethylamine salt, pyridine salt, picoline salt, dicyclohexylamine salt etc.) and the like.

Compounds (I) to (III) may be a tautomer. Examples of the tautomer of compound (III) include a compound represented by the formula (III'):

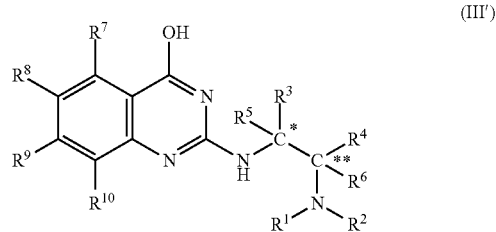

(III')

wherein each symbol is as defined above,
and the like.

In compounds (I) to (X), each group is preferably in the following embodiment.

$R^1$ and $R^2$
are preferably the same or different and each is a lower alkyl group optionally having substituent(s), an aralkyl group optionally having substituent(s) or an aryl group optionally having substituent(s);

are more preferably the same or different and each is a lower alkyl group optionally having substituent(s);
are further more preferably the same or different and each is an alkyl group having 1 to 6 carbon atoms and optionally having substituent(s);
are still more preferably the same or different and each is an alkyl group having 1 to 6 carbon atoms; and are particularly preferably methyl.

Ring A is
preferably an imidazole ring condensed with a benzene ring optionally having substituent(s), or a pyrimidin-4-one ring condensed with a benzene ring optionally having substituent(s);
more preferably an imidazole ring condensed with a benzene ring optionally having 1 to 3 halogen atoms, or a pyrimidin-4-one ring condensed with a benzene ring optionally having 1 to 3 halogen atoms.

$R^3$ and $R^4$ in combination form, together with the carbon atoms they are respectively bonded to,
preferably a homocycle optionally having substituent(s), or a heterocycle optionally having substituent(s) (the homocycle and heterocycle are optionally condensed with an aromatic hydrocarbon ring);
more preferably a homocycle optionally having substituent(s) (the homocycle is optionally condensed with an aromatic hydrocarbon ring);
further more preferably a cycloalkane having 3 to 6 carbon atoms and optionally having substituent(s);
still more preferably a cycloalkane having 3 to 6 carbon atoms;
particularly preferably cyclohexane.

$R^5$ and $R^6$ are preferably both hydrogen atoms.

$R^7$, $R^8$, $R^9$ and $R^{10}$
are preferably the same or different and each is a hydrogen atom or a halogen atom; and
are more preferably the same or different and each is a hydrogen atom or a fluorine atom.

$R^{11}$, $R^{12}$, $R^{13}$ and $R^{14}$
are preferably the same or different and each is a hydrogen atom or a halogen atom; and
are more preferably the same or different and each is a hydrogen atom or a chlorine atom.

$R^{15}$, $R^{16}$ and $R^{17}$
are preferably the same or different and each is a hydrogen atom, a lower alkyl group optionally having substituent(s), an aralkyl group optionally having substituent(s), an aryl group optionally having substituent(s), a heteroaryl group optionally having substituent(s), a hetero atom optionally having substituent(s), and an electron withdrawing group; and are more preferably the same or different and each is a hydrogen atom or an aryl group optionally having substituent(s).

More preferably, $R^{15}$ and $R^{17}$ are both hydrogen atoms, and $R^{16}$ is an aryl group optionally having substituent(s).

Further more preferably, $R^{15}$ and $R^{17}$ are both hydrogen atoms, and $R^{16}$ is an aryl group having 6 to 10 carbon atoms and optionally having substituent(s).

Still more preferably, $R^{15}$ and $R^{17}$ are both hydrogen atoms, and $R^{16}$ is phenyl optionally having substituent(s).

Particularly preferably, $R^{15}$ and $R^{17}$ are both hydrogen atoms, and $R^{16}$ is phenyl.

EWG is
preferably an electron withdrawing group selected from a nitro group and —CONHCOR$^{21}$ wherein R$^{21}$ is as defined above;
more preferably an electron withdrawing group selected from a nitro group and —CONHCOR$^{21}$ wherein R$^{21}$ is a hydrogen atom, a lower alkyl group optionally having substituent(s), an aralkyl group optionally having substituent(s), an aryl group optionally having substituent(s) or a heteroaryl group optionally having substituent(s);
more preferably an electron withdrawing group selected from a nitro group and —CONHCOR$^{21}$ wherein R$^{21}$ is an aryl group optionally having substituent(s);
further more preferably an electron withdrawing group selected from a nitro group and —CONHCOR$^{21}$ wherein R$^{21}$ is aryl group having 6 to 10 carbon atoms and optionally having substituent(s);
still more preferably an electron withdrawing group selected from a nitro group and —CONHCOR$^{21}$ wherein R$^{21}$ is phenyl optionally having substituent(s);
particularly preferably an electron withdrawing group selected from a nitro group and —CONHCOR$^{21}$ wherein R$^{21}$ is phenyl optionally having 1 to 3 halogen atoms.

Nu is
preferably —CR$^{24}$(COR$^{25}$)(COR$^{26}$) or —CR$^{27}$(CN)$_2$ wherein R$^{24}$, R$^{25}$, R$^{26}$ and R$^{27}$ are as defined above;
more preferably —CR$^{24}$(COR$^{25}$)(COR$^{26}$) or —CR$^{27}$(CN)$_2$ wherein R$^{24}$ is a hydrogen atom, R$^{25}$ and R$^{26}$ are the same or different and each is a lower alkoxy group, and R$^{27}$ is a hydrogen atom;
still more preferably —CR$^{24}$(COR$^{25}$)(COR$^{26}$) or —CR$^{27}$(CN)$_2$ wherein R$^{24}$ is a hydrogen atom, R$^{25}$ and R$^{26}$ are the same or different and each is an alkoxy group having 1 to 6 carbon atoms, and R$^{27}$ is a hydrogen atom;
particularly preferably —CR$^{24}$(COR$^{25}$)(COR$^{26}$) or —CR$^{27}$(CN)$_2$ wherein R$^{24}$ is a hydrogen atom, R$^{25}$ and R$^{26}$ are both ethoxy, R$^{27}$ is a hydrogen atom.

$PG^1$ and $PG^2$
are preferably the same or different and each is —CO$_2$R$^{37}$ or —CONR$^{38}$R$^{39}$ wherein R$^{37}$, R$^{38}$ and R$^{39}$ are as defined above;
are more preferably the same or different and each is —CO$_2$R$^{37}$ wherein R$^{37}$ is as defined above;
are more preferably the same or different and each is —CO$_2$R$^{37}$ wherein R$^{37}$ is a lower alkyl group optionally having substituent(s);
are further more preferably the same or different and each is —CO$_2$R$^{37}$ wherein R$^{37}$ is an alkyl group having 1 to 6 carbon atoms and optionally having substituent(s);
are still more preferably the same or different and each is —CO$_2$R$^{37}$ wherein R$^{37}$ is an alkyl group having 1 to 6 carbon atoms; and
are particularly preferably the same or different and each is —CO$_2$R$^{37}$ wherein R$^{37}$ is a tert-butyl group.

$R^{34}$ and $R^{35}$ in combination form, together with the carbon atom they are bonded to,
preferably a ring having an electron withdrawing group and optionally having substituent(s) (the ring is optionally condensed with an aromatic hydrocarbon ring);
more preferably cyclopentanone, cyclohexanone, 1-indanone or 1,2,3,4-tetrahydro-1-oxonaphthalene, each of which optionally has substituent(s);
still more preferably 1,2,3,4-tetrahydro-1-oxonaphthalene optionally having substituent(s);
particularly preferably 1,2,3,4-tetrahydro-1-oxonaphthalene.

$R^{36}$ is
preferably a cyano group, a nitro group, —P(═O)R$^{40}$R$^{41}$, SO$_2$R$^{42}$, —CO$_2$R$^{43}$, —CONR$^{44}$R$^{45}$ or —COR$^{46}$ wherein R$^{40}$, R$^{41}$, R$^{42}$, R$^{43}$, R$^{44}$, R$^{45}$, and R$^{46}$ are as defined above;
more preferably —CO$_2$R$^{43}$ wherein R$^{43}$ is as defined above;
more preferably —CO$_2$R$^{43}$ wherein R$^{43}$ is a lower alkyl group optionally having substituent(s);

further more preferably —CO$_2$R$^{43}$ wherein R$^{43}$ is an alkyl group having 1 to 6 carbon atoms and optionally having substituent(s);
still more preferably —CO$_2$R$^{43}$ wherein R$^{43}$ is an alkyl group having 1 to 6 carbon atoms;
particularly preferably —CO$_2$R$^{43}$ wherein R$^{43}$ is methyl.

The optically active compound of compound (I) is compound (II).

When R$^3$ and R$^4$ in combination form, together with the asymmetric carbon atoms they are respectively bonded to, a cycloalkane having 3 to 6 carbon atoms and optionally having substituent(s), then R$^5$ and R$^6$ are preferably each a hydrogen atom and the absolute configuration of C* and C** are preferably both S-configurations or both R-configurations.

Preferable embodiment of compound (II) of the present invention include compound (III), which is a compound having a quinazolin-4-one skeleton.

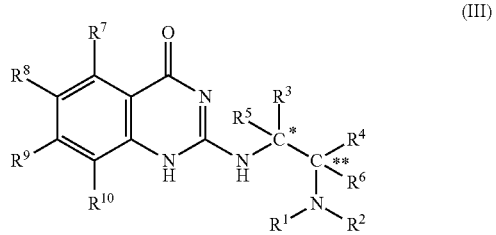
(III)

wherein each symbol is as defined above.

Compound (III) is preferably a compound wherein R$^1$ and R$^2$ are the same or different and each is a lower alkyl group optionally having substituent(s), an aralkyl group optionally having substituent(s) or an aryl group optionally having substituent(s);
R$^3$ and R$^4$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring);
R$^5$ and R$^6$ are both hydrogen atoms; and
R$^7$, R$^8$, R$^9$ and R$^{10}$ are the same or different and each is a hydrogen atom or a halogen atom.

Compound (III) is more preferably a compound wherein R$^1$ and R$^2$ are the same or different and each is a lower alkyl group optionally having substituent(s);
R$^3$ and R$^4$ in combination form, together with the carbon atoms they are respectively bonded to, a homocycle optionally having substituent(s) (the homocycle is optionally condensed with an aromatic hydrocarbon ring);
R$^5$ and R$^6$ are both hydrogen atoms; and
R$^7$, R$^8$, R$^9$ and R$^{18}$ are the same or different and each is a hydrogen atom or a halogen atom.

Compound (III) is more preferably a compound wherein R$^1$ and R$^2$ are the same or different and each is an alkyl group having 1 to 6 carbon atoms and optionally having substituent(s);
R$^3$ and R$^4$ in combination form, together with the carbon atoms they are respectively bonded to, a cycloalkane having 3 to 6 carbon atoms and optionally having substituent(s);
R$^5$ and R$^6$ are both hydrogen atoms;
R$^7$, R$^8$, R$^9$ and R$^{10}$ are the same or different and each is a hydrogen atom or a halogen atom; and
the absolute configuration of C* and C** are both S-configurations or both R-configurations.

Compound (III) is further more preferably a compound wherein
R$^1$ and R$^2$ are the same or different and each is an alkyl group having 1 to 6 carbon atoms;
R$^3$ and R$^4$ in combination form, together with the carbon atoms they are respectively bonded to, a cycloalkane having 3 to 6 carbon atoms;
R$^5$ and R$^6$ are both hydrogen atoms;
R$^7$, R$^8$, R$^9$ and R$^{10}$ are the same or different and each is a hydrogen atom or a halogen atom; and
the absolute configuration of C* and C** are both S-configurations or both R-configurations.

Compound (III) is still more preferably a compound wherein
R$^1$ and R$^2$ are both methyl;
R$^3$ and R$^4$ in combination form cyclohexane together with the carbon atoms they are respectively bonded to;
R$^5$ and R$^6$ are both hydrogen atoms;
R$^7$, R$^8$, R$^9$ and R$^{10}$ are the same or different and each is a hydrogen atom or a fluorine atom; and
the absolute configuration of C* and C** are both S-configurations or both R-configurations.

Compound (III) is particularly preferably an optically active compound represented by

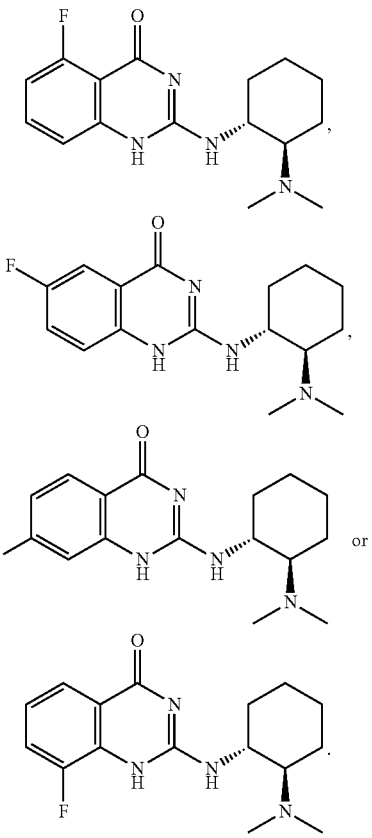

Preferable another embodiment of compound (II) of the present invention include compound (IV), which is a compound having a benzimidazole skeleton.

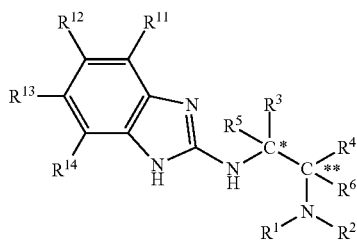

(IV)

wherein each symbol is as defined above.

Compound (IV) is preferably a compound wherein
$R^1$ and $R^2$ are the same or different and each is a lower alkyl group optionally having substituent(s), an aralkyl group optionally having substituent(s) or an aryl group optionally having substituent(s);
$R^3$ and $R^4$ in combination form, together with the carbon atoms they are respectively bonded to, a homocycle optionally having substituent(s), or a heterocycle optionally having substituent(s) (the homocycle and heterocycle are optionally condensed with an aromatic hydrocarbon ring);
$R^5$ and $R^6$ are both hydrogen atoms; and
$R^{11}$, $R^{12}$, $R^{13}$ and $R^{14}$ are the same or different and each is a hydrogen atom or a halogen atom.

Compound (IV) is more preferably a compound wherein
$R^1$ and $R^2$ are the same or different and each is a lower alkyl group optionally having substituent(s);
$R^3$ and $R^4$ in combination form, together with the carbon atoms they are respectively bonded to, a homocycle optionally having substituent(s) (the homocycle is optionally condensed with an aromatic hydrocarbon ring);
$R^5$ and $R^6$ are both hydrogen atoms; and
$R^{11}$, $R^{12}$, $R^{13}$ and $R^{14}$ are the same or different and each is a hydrogen atom or a halogen atom.

Compound (IV) is more preferably a compound wherein
$R^1$ and $R^2$ are the same or different and each is an alkyl group having 1 to 6 carbon atoms and optionally having substituent(s);
$R^3$ and $R^4$ in combination form, together with the carbon atoms they are respectively bonded to, a cycloalkane having 3 to 6 carbon atoms and optionally having substituent(s);
$R^5$ and $R^6$ are both hydrogen atoms;
$R^{11}$, $R^{12}$, $R^{13}$ and $R^{14}$ are the same or different and each is a hydrogen atom or a halogen atom; and
the absolute configuration of C* and C** are both S-configurations or both R-configurations.

Compound (IV) is further more preferably a compound wherein
$R^1$ and $R^2$ are the same or different and each is an alkyl group having 1 to 6 carbon atoms;
$R^3$ and $R^4$ in combination form, together with the carbon atoms they are respectively bonded to, a cycloalkane having 3 to 6 carbon atoms;
$R^5$ and $R^6$ are both hydrogen atoms;
$R^{11}$, $R^{12}$, $R^{13}$ and $R^{14}$ are the same or different and each is a hydrogen atom or a halogen atom; and
the absolute configuration of C* and C** are both S-configurations or both R-configurations.

Compound (IV) is still more preferably a compound wherein
$R^1$ and $R^2$ are both methyl;
$R^3$ and $R^4$ in combination form cyclohexane together with the carbon atoms they are respectively bonded to;
$R^5$ and $R^6$ are both hydrogen atoms;

$R^{11}$, $R^{12}$, $R^{13}$ and $R^{14}$ are the same or different and each is a hydrogen atom or a chlorine atom; and
the absolute configuration of C* and C** are both S-configurations or both R-configurations.

Compound (IV) is particularly preferably an optically active compound represented by

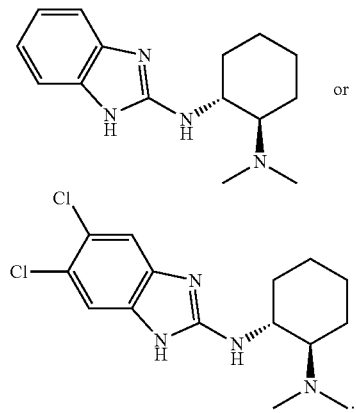

Compound (I) of the present invention can be produced according to the following Scheme 1.

Scheme 1

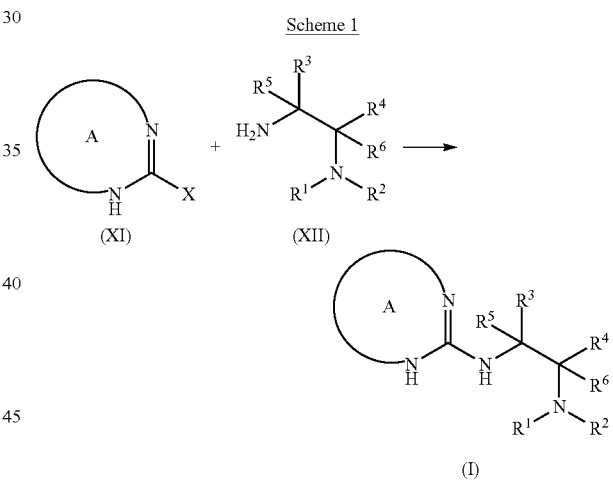

wherein X is a leaving group, and the other symbols are as defined above.

Examples of the "leaving group" for X include a halogen atom, an alkanesulfonyloxy group optionally having substituent(s) and optionally substituted arenesulfonyloxy group.

Examples of the halogen atom include a fluorine atom, a chlorine atom, a bromine atom and an iodine atom. Preferred are a chlorine atom and a bromine atom.

Examples of the alkanesulfonyloxy group of the alkanesulfonyloxy group optionally having substituent(s) include an alkanesulfonyloxy group having 1 to 6 carbon atoms such as methanesulfonyloxy, ethanesulfonyloxy and the like, and the like. Examples of the substituent include a halogen atom (e.g., a fluorine atom, a chlorine atom) and the like. Specific examples thereof include methanesulfonyloxy, trifluoromethanesulfonyloxy and the like.

Examples of the arenesulfonyloxy group of the arenesulfonyloxy group optionally having substituent(s) include an arenesulfonyloxy having 6 to 10 carbon atoms such as benzenesulfonyloxy and the like, and the like. Examples of the substituent include an alkyl group having 1 to 6 carbon atoms, a halogen atom (e.g., a fluorine atom, a chlorine atom) and the like. Specific examples thereof include benzenesulfonyloxy, p-toluenesulfonyloxy and the like.

Compound (I) can be produced by reacting the compound represented by the formula (XI) (hereinafter referred to as compound (XI)) with the compound represented by the formula (XII) (hereinafter referred to as compound (XII)) in the presence of a base, in a solvent.

The amount of compound (XII) to be used is generally 1.0 mol to 5.0 mol, preferably 1.0 mol to 2.0 mol, per 1 mol of compound (XI).

Examples of the base include organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; alkali metal carbonates such as sodium carbonate, potassium carbonate and the like; alkali metal hydrogencarbonates such as sodium hydrogencarbonate, potassium hydrogencarbonate and the like, and the like.

The amount of the base to be used is generally 1.0 mol to 5.0 mol, preferably 1.0 mol to 2.0 mol, per 1 mol of compound (XI).

The order of addition of compound (XI), compound (XII) and the base is not particularly limited, and they may be simultaneously or successively added to a solvent.

The solvent may be any as long as it does not inhibit the reaction, and for example, alcohol solvents such as methanol, ethanol, isoamyl alcohol and the like; halogenated solvents such as methylene chloride, chloroform, chlorobenzene, α,α,α-trifluorotoluene and the like; ether solvents such as methyl tert-butyl ether, 1,2-dimethoxyethane, tetrahydrofuran, 1,4-dioxane and the like; ester solvents such as ethyl acetate, isopropyl acetate, tert-butyl acetate; hydrocarbon solvents such as toluene, xylene; nitrile solvents such as acetonitrile and the like can be used alone or in a mixture. When a mixed solvent is used, they can be admixed at any ratio.

The amount of the solvent to be used is generally 0.5 L to 30 L, more preferably 1.0 L to 5.0 L, per 1 kg of compound (XI).

The reaction temperature is preferably near the boiling point of the solvent, and when isoamyl alcohol is used, it is 110° C. to 140° C.

While the reaction time varies depending on the kind of the starting material to be used (e.g., compound (XI), compound (XII)) and the reaction temperature, it is generally 1.0 hr to 200 hr, preferably 3.0 hr to 100 hr.

The obtained compound (I) can be isolated and purified according to a conventional method. For example, compound (I) can be isolated by pouring the reaction mixture into water to partition the mixture, and washing and concentrating the organic layer under reduced pressure; or by concentrating the reaction mixture. After isolation, the obtained product is purified, for example, by silica gel column chromatography, which is not to be construed as limitative.

Compound (XI) which is a starting material can be produced according to a known method (e.g., the method described in Bioorg. Med. Chem., 2000, 8, 2305; J. Med. Chem., 2006, 49, 3719; Bioorg. Med. Chem., 2003, 11, 2439; J. Med. Chem., 2007, 20, 2297 and the like).

Compound (XII) which is another starting material can be produced according to a known method (e.g., the method described in Tetrahedron, 57, 1765-1769 (2001)). For example, a compound represented by the formula (XIIa):

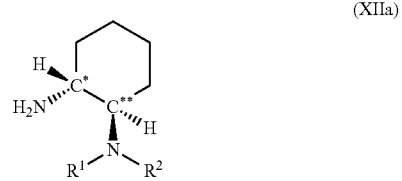

wherein each symbol is as defined above, which is preferably embodiment of the present invention, can be produced according to the method described in Tetrahedron Letters, 41, 8431-8434 (2000).

Compound (II) can also be produced according to Scheme 1.

Now, the production method of compound (VII) by an asymmetric conjugate addition reaction using compound (II) as an asymmetric catalyst is explained. The method is shown in the following Scheme 2.

Scheme 2

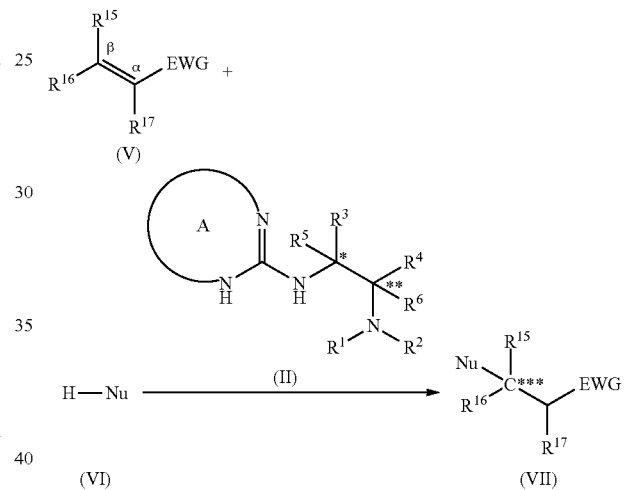

wherein each symbol is as defined above.

In this reaction, compound (VII) can be produced by conjugately adding nucleophilic reagent (VI) to compound (V) in the presence of compound (II), in a solvent or without solvent.

Since $C^{***}$ of compound (VII) is an asymmetric carbon, $R^{15}$ and $R^{16}$ of compound (V) are not the same groups.

Compound (VII) produced according to this reaction is optically active, wherein the optical purity is not particularly limited. An enantiomer excess measured by HPLC analysis using chiral column is generally not less than 50% e.e., preferably not less than 90% e.e.

In this reaction, the conjugate addition means, in compound (V), an addition reaction of nucleophilic reagent (VI) to a carbon not bonded to EWG (i.e., β-carbon) among from the carbons of the double bond conjugate-bonded to the electron withdrawing group for EWG.

The amount of compound (II) to be used is preferably 0.01 mol to 1.00 mol, more preferably 0.05 mol to 0.20 mol, per 1 mol of compound (V).

The amount of nucleophilic reagent (VI) to be used is generally 1 mol to 10 mol, preferably 1.2 mol to 3 mol, per 1 mol of compound (V).

This reaction can be carried out in a solvent or without solvent. The reaction without solvent is economically advantageous, and industrially advantageous from the aspect of high volume efficiency.

The solvent may be any as long as it does not inhibit the reaction, and for example, halogenated solvents such as methylene chloride, chloroform, chlorobenzene, α,α,α-trifluorotoluene and the like; ether solvents such as methyl tert-butyl ether, 1,2-dimethoxyethane, tetrahydrofuran, 1,4-dioxane and the like; ester solvents such as ethyl acetate, isopropyl acetate, tert-butyl acetate and the like; hydrocarbon solvents such as toluene, xylene and the like; nitrile solvents such as acetonitrile and the like can be used alone or in a mixture. From the aspect of superior yield and stereoselectivity, toluene or methylene chloride is preferably used. When a mixed solvent is used, they may be mixed at any ratio.

The amount of the solvent to be used is generally 1 L to 100 L, preferably 10 L to 30 L, per 1 kg of compound (V).

The order of addition of the reagents is not particularly limited, and compound (II), compound (V) and nucleophilic reagent (VI) may be simultaneously or successively added to a solvent.

The reaction temperature is generally −78° C. to 100° C., preferably 0° C. to 40° C.

While the reaction time varies depending on the reagents to be used and the reaction temperature, it is generally 0.1 hr to 100 hr.

The obtained compound (VII) can be isolated and purified according to a conventional method. For example, compound (VII) can be isolated by pouring the reaction mixture into water to partition the mixture, and washing and concentrating the organic layer under reduced pressure; or by concentrating the reaction mixture. After isolation, the obtained product is purified, for example, by silica gel column chromatography, which is not to be construed as limitative.

Compound (II) can be easily separated and recovered during isolation and purification of compound (VII). For example, since basic amine is present in compound (II), compound (II) can be separated from compound (VII) during extraction by transferring compound (II) in the form of a salt into the aqueous layer by treating the reaction mixture with an aqueous acidic solution (e.g., hydrochloric acid, nitric acid, sulfuric acid etc.). After neutralization of the aqueous solution, it is extracted with an organic solvent (e.g., ethyl acetate, toluene, chloroform, methylene chloride etc.) to recover compound (II). Compound (II) may also be separated and recovered by silica gel column chromatograph.

Compound (II) separated and recovered in this manner can be re-used for this reaction. That is, since compound (II) is non-metal, degradation of catalytic activity as observed in metal catalysts etc. does not occur easily, and compound (II) can be re-used as many times as desired upon recovery, which is economically advantageous.

Compound (V) which is a starting material can be produced according to a known method, for example, by subjecting a carbonyl compound represented by the following formula (XIII) and an active methylene compound represented by the following formula (XIV) to dehydration condensation.

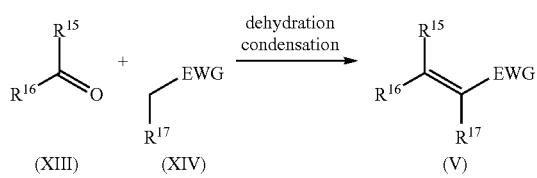

(XIII)  (XIV)  (V)

wherein each symbol is as defined above.

Examples of the dehydration condensation include aldol condensation, Knoevenagel reaction, Perkin reaction and the like, and modification of these methods.

In addition, trans-β-nitrostyrene and the like, which are preferable examples of compound (V), may be commercially available products.

Nucleophilic reagent (VI) which is a starting material can be produced according to a known method, for example, the method described in Tetrahedron Letters, 39, 8013-8016 (1998), Bull. Chem. Soc. Jpn., 61, 4029-4035 (1988) and the like. In addition, diethyl malonate and the like, which are preferable examples of nucleophilic reagent (VI), may be commercially available products.

Compound (VII) is useful as an intermediate for synthesizing amines, amino acids, medicaments, agricultural chemicals, food additives and the like. For example, ethyl (R)-3-(3-cyclopentyl-4-methoxyphenyl)-2-ethoxycarbonyl-4-nitrobutyrate, which is one example of compound (VII), can be converted to (R)-Rolipram (antidepressant) according to the method described in Journal of the American Chemical Society, vol. 124, No. 44, p. 13097-13105 (2002).

Next, The production method of compound (X) by an asymmetric hydrazination reaction using compound (II) as an asymmetric catalyst is explained. This reaction is shown in the following Scheme 3.

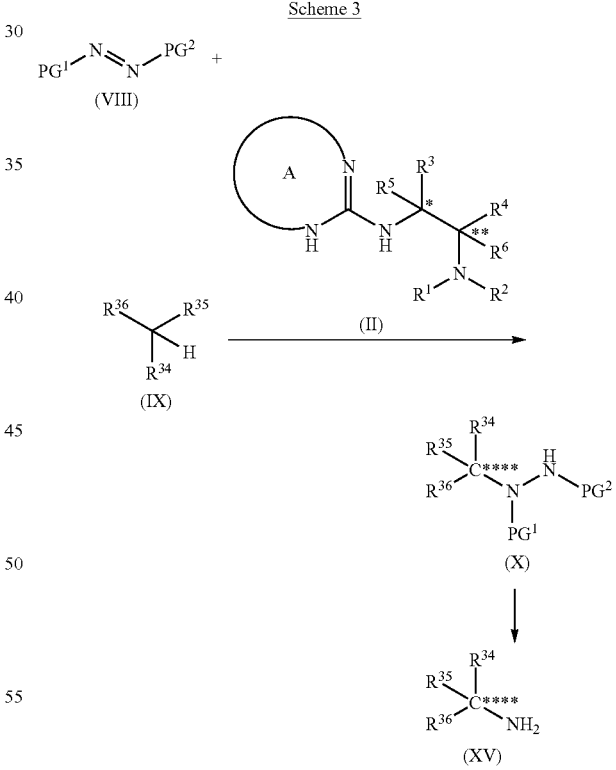

wherein each symbol is as defined above.

In this reaction, compound (X) can be produced by nucleophilically adding compound (IX) to compound (VIII) in the presence of compound (II).

Since C**** of compound (X) is an asymmetric carbon, $R^{35}$ and $R^{36}$ of compound (IX) are not the same groups.

Compound (X) produced according to this reaction is optically active, wherein the optical purity is not particularly limited. An enantiomer excess measured by HPLC analysis using chiral column is generally not less than 63% e.e., preferably not less than 76% e.e.

The amount of compound (II) to be used is preferably 0.01 mol to 1.00 mol, more preferably 0.05 mol to 0.20 mol, per 1 mol of compound (VIII).

The amount of compound (IX) to be used is generally 1 mol to 2 mol, preferably 1 mol to 1.1 mol, per 1 mol of compound (VIII).

This reaction can be carried out in a solvent or without solvent. The reaction without solvent is economically advantageous, and industrially advantageous from the aspect of high volume efficiency.

The solvent may be any as long as it does not inhibit the reaction, for example, halogenated solvents such as methylene chloride, chloroform, chlorobenzene, α,α,α-trifluorotoluene and the like; ether solvents such as diethyl ether, methyl tert-butyl ether, 1,2-dimethoxyethane, tetrahydrofuran, 1,4-dioxane and the like; ester solvents such as ethyl acetate, isopropyl acetate, tert-butyl acetate and the like; hydrocarbon solvents such as hexane, toluene, xylene and the like; nitrile solvents such as acetonitrile and the like can be used alone or in a mixture. From the aspect of superior yield and stereoselectivity, toluene, methylene chloride, diethyl ether or hexane is preferably used. When a mixed solvent is used, they may be mixed at any ratio.

The amount of the solvent to be used is generally 1 L to 100 L, preferably 10 L to 50 L, per 1 kg of compound (VIII).

In this reaction, the order of addition of the reagents is not particularly limited, compound (II), compound (VIII) and compound (IX) may be simultaneously or successively added to a solvent.

While the reaction temperature varies depending on the reagents to be used, it is generally −78° C. to 100° C., preferably −78° C. to 0° C.

While the reaction time varies depending on the reagents to be used and the reaction temperature, it is generally 25 hr 5 to 100 hr.

The obtained compound (X) can be isolated and purified according to a conventional method. For example, compound (X) can be isolated by pouring the reaction mixture into water to partition the mixture, and washing and concentrating the organic layer under reduced pressure; or by concentrating the reaction mixture. After isolation, the obtained product is purified, for example, by silica gel column chromatography, which is not to be construed as limitative.

Compound (II) can be easily separated and recovered during isolation and purification of compound (X). For example, since basic amine is present in compound (II), compound (II) can be separated from compound (X) during extraction by transferring compound (II) in the form of a salt into the aqueous layer by treating the mixture with an aqueous acidic solution (e.g., hydrochloric acid, nitric acid, sulfuric acid etc.). After neutralization of the aqueous solution, it is extracted with an organic solvent (e.g., ethyl acetate, toluene, chloroform, methylene chloride etc.) to recover compound (II). Compound (II) may also be separated and recovered by silica gel column chromatograph.

Compound (II) separated and recovered in this manner can be re-used for this reaction. That is, since compound (II) is non-metal, degradation of catalytic activity as observed in metal catalysts etc. does not occur easily, and compound (II) can be re-used as many times as desired upon recovery, which is economically advantageous.

Compound (X) can be converted into compound (XV) according to a method known per se, for example, according to the method described in 1) Angew. Chem. Int. Ed. 2002, 41, 1790-1793, or 2) J. Am. Chem. Soc. 2004, 126, 8120-8121.

That is, compound (XV) can be produced, for example, by reacting compound (X) with a base or an acid in a solvent or without solvent to remove the protecting group ($PG^1$ and $PG^2$), and then subjecting the resulting compound to a catalytic reduction or reacting the resulting compound with zinc powder to reduce the nitrogen-nitrogen bond. The reaction can be carried out according to the reaction conditions described in the above-mentioned document, and therefore, the detail of the reaction conditions is omitted.

Compound (VIII) which is a starting material may be commercially available product.

Compound (IX) which is a starting material can be selected, without limitation, from known compounds, depending on the object.

Compound (X) and compound (XV) may be useful as an intermediate for synthesizing amines, amino acids, medicaments, agricultural chemicals, food additives and the like.

EXAMPLES

The present invention is explained more specifically in the following by referring to Examples, which are not to be construed as limitative.

Example 1

(R,R)-trans-2-[2-(N,N-dimethylamino)cyclohexylamino]benzimidazole

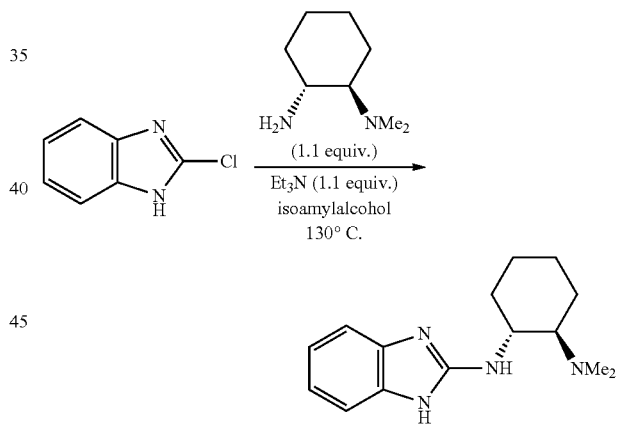

2-Chlorobenzimidazole (304.8 mg, 2.0 mmol), (1R,2R)—$N^1,N^1$-dimethylcyclohexane-1,2-diamine (307.8 mg, 2.2 mmol) and triethylamine (0.3 mL, 2.2 mmol) were stirred in isoamyl alcohol (1.0 mL) at 130° C. for 41 hr. Then, to the reaction mixture was added aqueous sodium hydrogencarbonate, and the mixture was extracted with ethyl acetate. The organic layer was dried over potassium carbonate, filtrated, and concentrated under reduced pressure. The residue was purified by silica gel column chromatography (chloroform containing ammonia/chloroform/methanol=9/0/1→0/9/1) to give the title compound (303 mg) as a white solid. The yield was 59%.

mp. 230-232° C.;

$[\alpha]_D^{34}$=−24.0 (c 0.69, $CDCl_3$);

$^1$H-NMR (δ, $CDCl_3$): 7.40-7.26 (m, 2H), 7.04 (d, J=5.7 Hz, 1H), 7.03 (d, J=5.7 Hz, 1H), 5.45 (s, 1H), 3.42 (ddd, $J_1=J_2$=10.5 Hz, $J_3$=3.9 Hz, 1H), 2.76-2.64 (m, 1H), 2.36 (ddd, $J_1=J_2=10.5$ Hz, $J_3=2.8$ Hz, 1H), 2.24 (s, 6H), 1.94-1.77 (m, 2H), 1.77-1.65 (m, 1H), 1.48-1.31 (m, 1H), 1.31-1.11 (m, 3H);

IR (KBr): 3265;

LRMS [FAB+] m/z=259 (M+H$^+$);

Anal. Calcd for $C_{15}H_{22}N_4$: C, 69.73; H, 8.58; N, 21.69. Found: C, 69.74; H, 8.35; N, 21.71.

Example 2

(R,R)-trans-2-[2-(N,N-dimethylamino)cyclohexylamino]-5,6-dichlorobenzimidazole

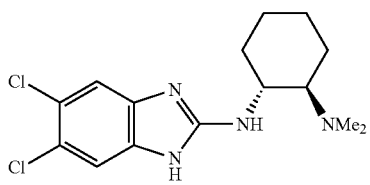 [SMILES: CN(C)[C@@H]1CCCC[C@H]1Nc1nc2cc(Cl)c(Cl)cc2[nH]1]

In the same manner as in Example 1 except that 2-chloro-5,6-dichlorobenzimidazole was used instead of 2-chlorobenzimidazole, the title compound (181 mg) was obtained as a brownish solid. The yield was 30%.

$^1$H-NMR (δ, CDCl$_3$): 7.29 (s, 2H), 5.47 (s, 1H), 3.46-3.35 (m, 1H), 2.61-2.51 (m, 1H), 2.42-2.31 (m, 1H), 2.27 (s, 6H), 1.95-1.78 (m, 2H), 1.78-1.64 (m, 1H), 1.41-1.10 (m, 4H);

IR (KBr): 3308;

LRMS (FAB$^+$) m/z=327 (M+H$^+$);

Anal. Calcd for: C, 55.05; H, 6.16; N, 17.12. Found: C, 54.94; H, 6.29; N, 16.83.

Example 3

(R,R)-trans-2-[2-(N,N-dimethylamino)cyclohexylamino]quinazolin-4-one

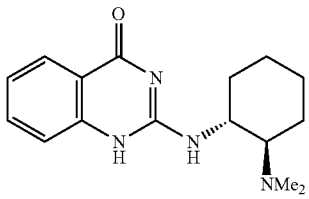

In the same manner as in Example 1 except that 2-chloroquinazolin-4-one was used instead of 2-chlorobenzimidazole, the title compound (327 mg) was obtained. The yield was 68%.

mp: 117-121° C.;

$[α]_D^{30}=-29.46$ (c=0.93, CHCl$_3$);

$^1$H-NMR (δ, CDCl$_3$): 8.10 (dd, $J_1=7.94$ Hz, $J_2=1.44$ Hz, 1H), 7.52 (ddd, $J_1=J_2=7.94$ Hz, $J_3=1.44$ Hz, 1H), 7.22 (d, 7.94 Hz, 1H), 7.12 (dd, $J_1=J_2=7.94$ Hz, 1H), 3.69-3.57 (m, 1H), 2.52 (ddd, $J_1=J_2=10.26$ Hz, $J_3=2.92$ Hz, 1H), 2.45-2.32 (m, 1H), 2.36 (s, 6H), 1.96-1.87 (m, 1H), 1.87-1.69 (m, 2H), 1.52-1.16 (m, 4H);

IR (KBr): 3254, 1679, 1606;

LRMS (FAB$^+$) m/z=287 (M+H$^+$).

Example 4

(R,R)-trans-2-[2-(N,N-dimethylamino)cyclohexylamino]-5-fluoroquinazolin-4-one

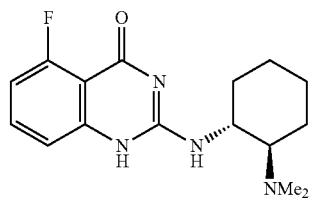 [SMILES: CN(C)[C@@H]1CCCC[C@H]1Nc1nc(=O)c2c(F)cccc2[nH]1]

In the same manner as in Example 1 except that 2-chloro-5-fluoroquinazolin-4-one was used instead of 2-chlorobenzimidazole, the title compound was obtained.

$^1$H-NMR (δ, CDCl$_3$): 7.43 (ddd, $J_1=J_2=8.0$, $J_3=5.5$ Hz, 1H), 7.04 (d, J=8.0 Hz, 1H), 6.73 (dd, $J_1=10.5$, $J_2=8.0$ Hz, 1H), 6.23 (bs, 1H), 3.60-3.51 (m, 1H), 2.51 (ddd, $J_1=J_2=10.5$, $J_3=3.3$ Hz), 2.41-2.30 (m, 1H), 2.38 (s, 6H), 1.97-1.89 (m, 1H), 1.80-1.72 (m, 1H), 1.42-1.18 (m, 4H);

IR (KBr): 3290, 1682, 1614;

LRMS (FAB$^+$) m/z=287 (M+H$^+$).

Example 5

(R,R)-trans-2-[2-(N,N-dimethylamino)cyclohexylamino]-6-fluoroquinazolin-4-one

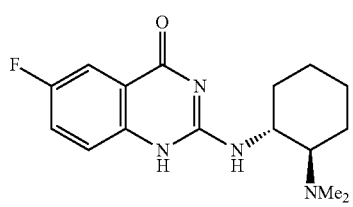 [SMILES: CN(C)[C@@H]1CCCC[C@H]1Nc1nc(=O)c2cc(F)ccc2[nH]1]

In the same manner as in Example 1 except that 2-chloro-6-fluoroquinazolin-4-one was used instead of 2-chlorobenzimidazole, the title compound was obtained.

$^1$H-NMR (δ, CDCl$_3$): 7.74 (dd, $J_1=8.76$, $J_2=2.92$, 1H), 7.34-7.23 (m, 2H), 6.14 (bs, 1H), 3.56-3.40 (m, 1H), 2.58-2.46 (m, 1H), 2.46-2.27 (m, 1H), 2.42 (s, 6H), 2.00-1.89 (m, 1H), 1.89-1.82 (m, 1H), 1.45-1.15 (m, 4H);

LRMS (FAB$^+$) m/z=305 (M+H$^+$).

Example 6

(R,R)-trans-2-[2-(N,N-dimethylamino)cyclohexylamino]-7-fluoroquinazolin-4-one

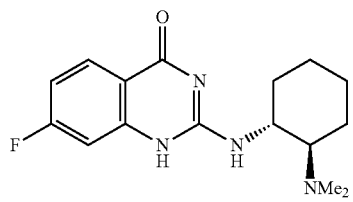

In the same manner as in Example 1 except that 2-chloro-7-fluoroquinazolin-4-one was used instead of 2-chlorobenzimidazole, the title compound was obtained.

$^1$H-NMR (6, CDCl$_3$): 8.09 (dd, J$_1$=8.50 Hz, J$_2$=6.46 Hz, 1H), 6.92 (dd, J$_1$=10.36 Hz, J$_2$=2.34 Hz, 1H), 6.85 (ddd, J$_1$=J$_2$=8.50 Hz, J$_3$=2.34 Hz, 1H), 3.51-3.40 (m, 1H), 2.47 (ddd, J$_1$=J$_2$=10.98 Hz, J$_3$=3.66 Hz), 2.38 (s, 6H), 2.42-2.31 (m, 1H), 1.99-1.89 (m, 1H), 1.89-1.81 (m, 1H), 1.81-1.70 (m, 1H), 1.40-1.16 (m, 4H);

IR (KBr): 3254, 1680;

LRMS (FAB$^+$) m/z=305 (M+H$^+$).

Example 7

(R,R)-trans-2-[2-(N,N-dimethylamino)cyclohexylamino]-8-fluoroquinazolin-4-one

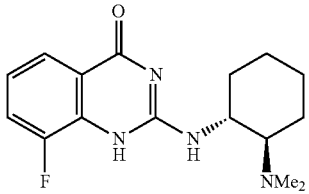 [SMILES: CN(C)[C@@H]1CCCC[C@H]1Nc1nc(=O)c2cccc(F)c2[nH]1]

In the same manner as in Example 1 except that 2-chloro-8-fluoroquinazolin-4-one was used instead of 2-chlorobenzimidazole, the title compound was obtained.

$^1$H-NMR (δ, CDCl$_3$): 7.88 (d, J=7.9 Hz, 1H), 7.32-7.20 (m, 1H), 7.04 (ddd, J$_1$=J$_2$=7.90 Hz, J$_3$=4.62 Hz, 1H), 6.56 (bs, 1H), 3.66-3.50 (m, 1H), 2.65-2.50 (m, 1H), 2.44 (s, 6H), 2.01-1.89 (m, 1H), 1.89-1.71 (m, 1H), 1.55-1.14 (m, 4H);

IR (KBr): 3257, 1682;

LRMS (FAB$^+$) m/z=305 (M+H$^+$).

Example 8 ethyl (S)-2-ethoxycarbonyl-4-nitro-3-phenylbutyrate

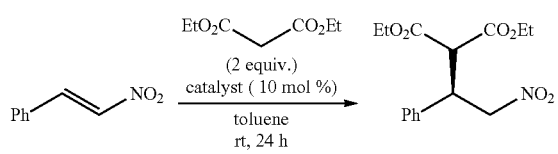 [SMILES: O=[N+]([O-])/C=C/c1ccccc1 ; CCOC(=O)CC(=O)OCC ; CCOC(=O)C(C(=O)OCC)[C@@H](C[N+](=O)[O-])c1ccccc1]

trans-β-Nitrostyrene (34.3 mg, 0.23 mmol), diethyl malonate (0.065 mL, 0.46 mmol) and the compound (10 mol %) shown in the following Table 1 as an asymmetric catalyst were stirred in toluene (0.4 mL) at room temperature. The reaction mixture was purified by silica gel column chromatography (n-hexane/ethyl acetate=95/5→90/10→80/20) to give the title compound.

$^1$H-NMR (6, CDCl$_3$): 7.34-7.23 (m, 5H), 4.95-4.83 (m, 2H), 4.27-4.18 (m, 3H), 4.01 (q, J=7.08 Hz), 3.82 (d, J=9.28 Hz), 1.26 (t, J=7.08 Hz), 1.05 (t, J=7.08 Hz);

HPLC [Chiralcel AD-H, hexane/EtOH=9/1, 1 mL/min, 254 nm, retention times: (major) 11.7 min, (minor) 15.5 min].

TABLE 1

| Example | Reaction Time | Yield (%) | Optical Purity (% ee) |
|---|---|---|---|
| 1 | 24 hr | 70 | 77 |
| 2 | 7 hr | 71 | 85 |
| 3 | 24 hr | 70 | 85 |
| 4 | 24 hr | 69 | 84 |
| 5 | 48 hr | 95 | 78 |
| 6 | 48 hr | 95 | 82 |
| 7 | 48 hr | 95 | 76 |

Production Example 1

(E)-N-cinnamoyl-2-fluorobenzamide

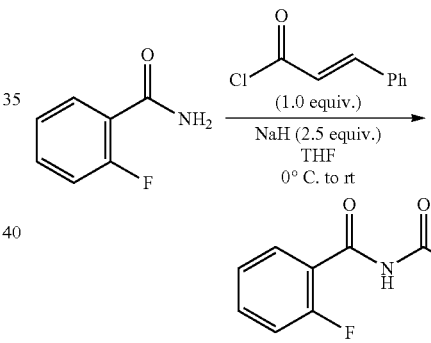

Under an argon atmosphere, 2-fluorobenzamide (1.41 g, 10.0 mmol), sodium hydride (60% dispersion in mineral oil, 1.04 g, 25.0 mmol) and tetrahydrofuran (3 mL) were stirred under ice-cooling. A solution of cinnamoyl chloride (1.68 g, 10.0 mmol) in tetrahydrofuran (3 mL) was added thereto, and the mixture was warmed to room temperature. After stirring for 1 hr, to the mixture was added diluted hydrochloric acid, and the mixture was extracted with ethyl acetate. The organic layer was washed with aqueous sodium hydrogencarbonate, dried over magnesium sulfate, and concentrated under reduced pressure. The residue was crystallized from ethyl acetate/n-hexane to give the title compound (1.91 g) as a white solid. The yield was 70%.

$^1$H-NMR (δ, CDCl$_3$): 8.97 (d, J=12.6, 1H), 8.10 (ddd, J$_1$=J$_2$=7.75 Hz, J$_3$=1.9 Hz, 1H), 7.92 (d, J=15.5 Hz, 1H), 7.74 (d, J=15.5, 1H), 7.70-7.54 (m, 3H), 7.47-7.32 (m, 4H), 7.21 (dd, J$_1$=12.0, J$_2$=8.60 Hz, 1H);

IR (KBr): 3368, 1708, 1677;

LRMS (FAB+) m/z=270 (M+H$^+$);

Anal Calcd for C$_{16}$H$_{12}$FNO$_2$: C, 71.37; H, 4.49; N, 5.20. Found: C, 71.53; H, 4.52; N, 5.24.

Example 9

(S)-4,4-dicyano-N-(2-fluorobenzoyl)-3-phenyl-butanamide

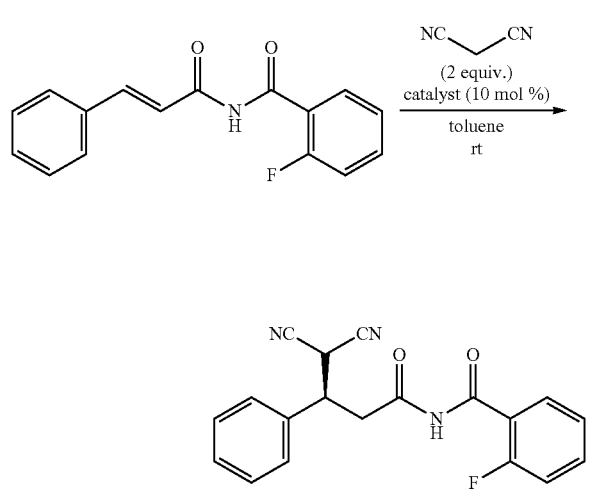

(E)-N-Cinnamoyl-2-fluorobenzamide (26.9 mg, 0.1 mmol), malononitrile (13.2 mg, 0.2 mmol) and the compound (10 mol %) shown in the following Table 2 as an asymmetric catalyst were stirred in toluene (1.0 mL) at room temperature for 27 hr. The reaction mixture was purified by silica gel column chromatography (n-hexane/ethyl acetate=4/1) to give the title compound as a white solid.

$^1$H-NMR (δ, CDCl$_3$): 9.06 (d, J=14.35 Hz), 8.06 (dd, J$_1$=J$_2$=7.75, 1H), 7.62 (dd, J$_1$=10.56, J$_2$=4.82 Hz, 1H), 7.51-7.37 (m, 5H), 7.35 (dd, J$_1$=J$_2$=7.45, 1H), 7.21 (dd, J$_1$=12.32 Hz, J$_2$=8.28 Hz), 4.59 (d, J=5.7 Hz, 1H), 3.89 (d, t, J$_1$=7.22 Hz, J$_2$=5.70 Hz, 1H), 3.73 (d, J=7.22 Hz, 2H);

$^{13}$C NMR (δ, CDCl$_3$): 172.4, 162.0 (d, J=3.60 Hz), 160.6 (d, J=249.5 Hz), 136.0, 135.8 (d, J=10.8 Hz), 132.4, 129.3, 129.2, 128.1, 125.5 (d, J=2.4 Hz), 124.3 (d, J=9.60 Hz), 116.6 (d, J=24.0 Hz), 114.6 (d, J=37.1 Hz), 41.4, 40.2, 28.8;

IR (KBr): 3245, 1730, 1675;

LRMS (FAB+) m/z=336 (M+H$^+$);

HPLC [Chiralcel OD-H, hexane/2-propanol=7/3, 1.0 mL/min, retention times: (minor) 20.4 min, (major) 26.6 min.].

TABLE 2

| Example | Reaction Time | Yield (%) | Optical Purity (% ee) |
|---------|---------------|-----------|----------------------|
| 1 | 81 hr | 90 | 80 |
| 2 | 27 hr | 91 | 77 |
| 3 | 81 hr | 84 | 69 |
| 4 | 81 hr | 76 | 67 |
| 5 | 81 hr | 82 | 72 |
| 6 | 81 hr | 93 | 72 |
| 7 | 81 hr | 94 | 66 |

Production Example 2 methyl 1,2,3,4-tetrahydro-1-oxonaphthalene-2-carboxylate

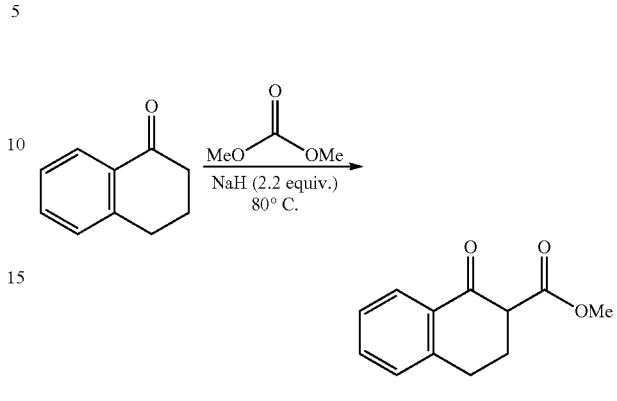

Under an argon atmosphere, a mixture of sodium hydride (60% dispersion in mineral oil, 887 mg, 22.0 mmol), dimethyl carbonate (15 mL) and 3,4-dihydronaphthalen-1(2H)-one (1.46 g, 10.0 mmol) was stirred at 80° C. for 3.5 hr. The reaction mixture was quenched with diluted hydrochloric acid, and extracted with ethyl acetate. The organic layer was dried over sodium carbonate, filtrated, and concentrated under reduced pressure. The residue was purified by silica gel column chromatography (n-hexane/ethyl acetate=1/0-5/1) to give the title compound as a white solid.

Example 10 methyl N,N'-bis(tert-butyloxycarbonyl)-2-hydrazino-[1,2,3,4-tetrahydro-1-oxonaphthalene]-2-carboxylate

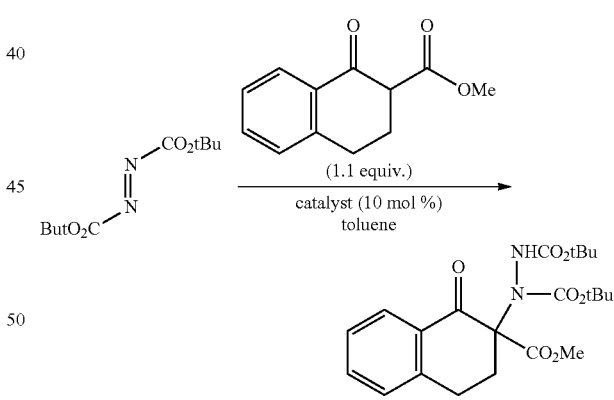

To a solution of di-tert-butyl azodicarboxylate (47.8 mg, 0.21 mmol) in toluene (2.0 mL) were added methyl 1,2,3,4-tetrahydro-1-oxonaphthalene-2-carboxylate (46.7 mg, 0.23 mmol) and the compound (10 mol %) shown in the following Table 3 as an asymmetric catalyst at room temperature. The mixture was stirred at room temperature for 5 hr, and purified by silica gel column chromatography (n-hexane/ethyl acetate=90/10→50/50) to give the title compound as a white solid.

Rf 0.53 (silica gel, hexane/EtOAc=5/1);

HPLC [Chiralcel OD-H, hexane/EtOAc=95/5, 0.5 mL/min, 254 nm, retention times:
(major) 15.5 min, (minor) 18.6 min.].

TABLE 3

| Example | Yield (%) | Optical Purity (% ee) |
|---------|-----------|------------------------|
| 1 | 84 | 88 |
| 2 | 96 | 77 |
| 3 | 35 | 99 |
| 4 | 52 | 97 |
| 5 | 43 | 99 |
| 6 | 49 | 99 |
| 7 | 27 | 99 |

INDUSTRIAL APPLICABILITY

According to the present invention, compound (VII) can be produced in a high yield and with high stereoselectivity by conjugately adding nucleophilic reagent (VI) to compound (V) using compound (II) as an asymmetric catalyst.

In addition, compound (X) can be produced in a high yield and with high stereoselectivity by adding compound (IX) to compound (VIII) using compound (II) as an asymmetric catalyst. The obtained compound (X) can be easily converted into compound (XV) by the cleavage of the nitrogen-nitrogen bond.

In addition, since compound (II) is non-metallic, it does not require treatments of metal waste liquid and the like, and therefore, it is an environmentally-friendly catalyst. Moreover, since it is non-metallic, the compound can be recovered and reused easily.

The invention claimed is:

1. A compound of formula (IV)

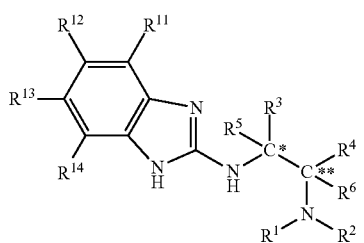

(IV)

wherein $R^1$ and $R^2$ are the same or different and each is a lower alkyl group optionally having substituent(s), an aralkyl group optionally having substituent(s), or an aryl group optionally having substituent(s), or $R^1$ and $R^2$ in combination form, together with the nitrogen atom they are bonded to, a heterocycle selected from pyrrolidine, piperidine, morpholine, thiomorpholine, and piperazine, each optionally having substituent(s), wherein the heterocycle is optionally condensed with an aromatic hydrocarbon ring, $R^3$ and $R^4$ are the same or different and each is a lower alkyl group optionally having substituent(s), a lower alkenyl group optionally having substituent(s), a lower alkynyl group optionally having substituent(s), an aralkyl group optionally having substituent(s), or an aryl group optionally having substituent(s), or $R^3$ and $R^4$ in combination form, together with the carbon atoms they are respectively bonded to, a homocycle optionally having substituent(s), or a heterocycle selected from pyrrolidine, piperidine, morpholine, thiomorpholine, and piperazine, each optionally having substituent(s), wherein the homocycle and heterocycle are optionally condensed with an aromatic hydrocarbon ring, $R^5$ and $R^6$ are the same or different and each is a hydrogen atom or a lower alkyl group optionally having substituent(s), $R^{11}$, $R^{12}$, $R^{13}$ and $R^{14}$ are the same or different and each is a hydrogen atom, a halogen atom, a hydroxyl group, a lower alkyl group optionally having substituent(s), an aralkyl group optionally having substituent(s), an aryl group optionally having substituent(s) or a lower alkoxy group optionally having substituent(s), and C* and C** are each an asymmetric carbon, or a salt thereof.

2. The compound of claim 1, which is represented by the following formula:

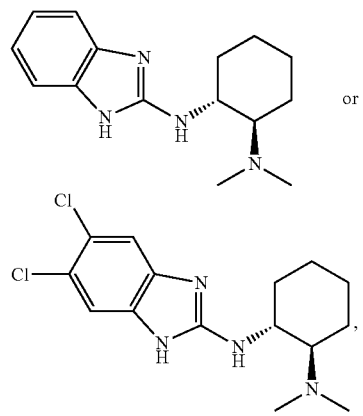

or a salt thereof.

3. The compound of claim 1, wherein $R^1$ and $R^2$ are the same or different and each is a lower alkyl group optionally having substituent(s), a tautomer thereof or a salt thereof.

4. The compound of claim 1, wherein $R^3$ and $R^4$ in combination form, together with the carbon atoms they are respectively bonded to, a cycloalkane having 3 to 6 carbon atoms and optionally having substituent(s), a tautomer thereof or a salt thereof.

5. The compound of claim 1, wherein $R^5$ and $R^6$ are both hydrogen atoms, a tautomer thereof or a salt thereof.

6. The compound of claim 1, wherein C* and C** are both R-configurations or both S-configurations, a tautomer thereof or a salt thereof.

7. A method of producing a compound of formula (VII):

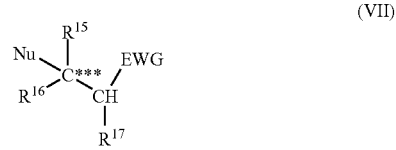

(VII)

wherein $R^{15}$, $R^{16}$ and $R^{17}$ are the same or different and each is a hydrogen atom, a lower alkyl group optionally having substituent(s), an aralkyl group optionally having substituent(s), an aryl group optionally having substituent(s), a heteroaryl group selected from 2- or 3-thienyl, 2- or 3-furyl, 1-, 2-, or 3-pyrrolyl, 1-, 2-, 4-, or 5-imidazolyl, 2-, 4-, or 5-oxazolyl, 2-, 4-, or 5-thiazolyl, 1-, 3-, 4-, or 5-pyrazolyl, 3-, 4-, or 5-isoxazolyl, 3-, 4-, or 5-isothiazolyl, 1,2,4-triazol-1-, 3-, 4-, or 5-yl, 1,2,3-triazol-1-, 2-, or 4-yl, 1H-tetrazol-1- or 5-yl, 2H-tetrazol-2- or 5-yl, 2-, 3-, or 4-pyridyl, 2-, 4-, or 5-pyrimidinyl, 1-, 2-, 3-, 4-, 5-, 6-, or 7-indolyl, 2-, 3-, 4-, 5-, 6-, or 7-benzofuryl, 2-, 3-, 4-, 5-, 6-, or 7-benzothienyl, 1-, 2-, 4-, 5-, 6-, or 7-benzimidazolyl, 2-, 3-, 4-, 5-, 6-, 7-, or 8-quinolyl, and 1-, 3-, 4-, 5-, 6-, 7-, or 8-isoquinolyl, each optionally having substituent(s), a hetero atom optionally having substituent(s), or an electron withdrawing group, or $R^{16}$ and $R^{17}$ in combination form, together with the carbon atoms they are respectively bonded to, a homocycle optionally having substituent(s), or a heterocycle selected from 5,6-dihydro-2H-pyranyl, 3,4-dihydro-2H-pyranyl, 2,3- or 2,5-dihydrofuranyl, 2- or 3-pyrrolinyl, and 1,2,3,4- or 1,2,3,6-tetrahydropyridinyl, each optionally having substituent(s), wherein the homocycle and heterocycle are optionally condensed with an aromatic hydrocarbon ring, provided that $R^{15}$ and $R^{16}$ are not the same groups;

EWG is an electron withdrawing group selected from a nitro group, a cyano group, —$COR^{18}$, —$SO_2R^{19}$, —$COOR^{20}$, —$CONHCOR^{21}$ and —$PO(OR^{22})(OR^{23})$ wherein $R^{18}$, $R^{19}$, $R^{20}$, $R^{21}$, $R^{22}$ and $R^{23}$ are the same or different and each is a hydrogen atom, a lower alkyl group optionally having substituent(s), an aralkyl group optionally having substituent(s), an aryl group optionally having substituent(s) or a heteroaryl group selected from 2- or 3-thienyl, 2- or 3-furyl, 1-, 2-, or 3-pyrrolyl, 1-, 2-, 4-, or 5-imidazolyl, 2-, 4-, or 5-oxazolyl, 2-, 4-, or 5-thiazolyl, 1-, 3-, 4-, or 5-pyrazolyl, 3-, 4-, or 5-isoxazolyl, 3-, 4-, or 5-isothiazolyl, 1,2,4-triazol-1-, 3-, 4-, or 5-yl, 1,2,3-triazol-1-, 2-, or 4-yl, 1H-tetrazol-1- or 5-yl, 2H-tetrazol-2- or 5-yl, 2-, 3-, or 4-pyridyl, 2-, 4-, or 5-pyrimidinyl, 1-, 2-, 3-, 4-, 5-, 6-, or 7-indolyl, 2-, 3-, 4-, 5-, 6-, or 7-benzofuryl, 2-, 3-, 4-, 5-, 6-, or 7-benzothienyl, 1-, 2-, 4-, 5-, 6-, or 7-benzimidazolyl, 2-, 3-, 4-, 5-, 6-, 7-, or 8-quinolyl, and 1-, 3-, 4-, 5-, 6-, 7-, or 8-isoquinolyl, each optionally having substituent(s), or $R^{18}$ and $R^{15}$ or $R^{18}$ and $R^{17}$ in combination form, together with the carbon atoms they are respectively bonded to, a homocycle having an electron withdrawing group and optionally having substituent(s), wherein the homocycle is optionally condensed with an aromatic hydrocarbon ring;

Nu is —$CR^{24}(COR^{25})(COR^{26})$, —$CR^{27}(CN)_2$, —$OR^{28}$, —$SR^{29}$, —$NR^{30}R^{31}$ or —$C(NO_2)R^{32}R^{33}$ wherein $R^{24}$ is a hydrogen atom, a halogen atom, a hetero atom having substituent(s), a lower alkyl group optionally having substituent(s) or an aryl group optionally having substituent(s);

$R^{25}$ and $R^{26}$ are the same or different and each is a hydrogen atom, a lower alkyl group, a lower alkoxy group, a mono-lower alkylamino group or a di-lower alkylamino group, or $R^{24}$ and $R^{25}$ in combination form, together with the carbon atoms they are respectively bonded to, a homocycle optionally having substituent(s), or a heterocycle selected from tetrahydropyranonyl, tetrahydrofuranonyl, pyrrolidinyl, and piperidonyl, each optionally having substituent(s), wherein the homocycle and heterocycle are optionally condensed with an aromatic hydrocarbon ring;

$R^{27}$ is a hydrogen atom, a halogen atom, a hetero atom having substituent(s), a lower alkyl group optionally having substituent(s) or an aryl group optionally having substituent(s);

$R^{28}$, $R^{29}$, $R^{30}$, $R^{31}$, $R^{32}$ and $R^{33}$ are the same or different and each is a hydrogen atom, a lower alkyl group optionally having substituent(s), an aralkyl group optionally having substituent(s), an aryl group optionally having substituent(s) or a heteroaryl group selected from 2- or 3-thienyl, 2- or 3-furyl, 1-, 2-, or 3-pyrrolyl, 1-, 2-, 4-, or 5-imidazolyl, 2-, 4-, or 5-oxazolyl, 2-, 4-, or 5-thiazolyl, 1-, 3-, 4-, or 5-pyrazolyl, 3-, 4-, or 5-isoxazolyl, 3-, 4-, or 5-isothiazolyl, 1,2,4-triazol-1-, 3-, 4-, or 5-yl, 1,2,3-triazol-1-, 2-, or 4-yl, 1H-tetrazol-1- or 5-yl, 2H-tetrazol-2- or 5-yl, 2-, 3-, or 4-pyridyl, 2-, 4-, or 5-pyrimidinyl, 1-, 2-, 3-, 4-, 5-, 6-, or 7-indolyl, 2-, 3-, 4-, 5-, 6-, or 7-benzofuryl, 2-, 3-, 4-, 5-, 6-, or 7-benzothienyl, 1-, 2-, 4-, 5-, 6-, or 7-benzimidazolyl, 2-, 3-, 4-, 5-, 6-, 7-, or 8-quinolyl, and 1-, 3-, 4-, 5-, 6-, 7-, or 8-isoquinolyl, each optionally having substituent(s), or $R^{30}$ and $R^{31}$ in combination form, together with the nitrogen atom they are bonded to, a heterocycle selected from pyrrolidinyl, piperidinyl, morpholinyl, thiomorpholinyl, and piperazinyl, each optionally having substituent(s), wherein the heterocycle is optionally condensed with an aromatic hydrocarbon ring, or an azido group; and C*** an asymmetric carbon, or a salt thereof, which comprises conjugately adding a nucleophilic reagent represented by the formula (VI): H-Nu (VI) wherein Nu is as defined above, to a compound represented by the formula (V):

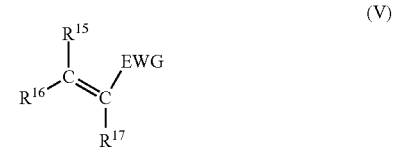

wherein each symbol is as defined above, or a salt thereof, in the presence of the compound of claim 1, a tautomer thereof or a salt thereof.

8. A method of producing a compound of formula (X):

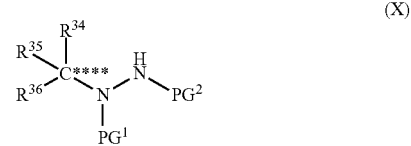

wherein $PG^1$ and $PG^2$ are the same or different and each is a protecting group, $R^{34}$ is a hydrogen atom, a lower alkyl group optionally having substituent(s), an aralkyl group optionally having substituent(s), an aryl group optionally having substituent(s) or a heteroaryl group selected from 2- or 3-thienyl, 2- or 3-furyl, 1-, 2-, or 3-pyrrolyl, 1-, 2-, 4-, or 5-imidazolyl, 2-, 4-, or 5-oxazolyl, 2-, 4-, or 5-thiazolyl, 1-, 3-, 4-, or 5-pyrazolyl, 3-, 4-, or 5-isoxazolyl, 3-, 4-, or 5-isothiazolyl, 1,2,4-triazol-1-, 3-, 4-, or 5-yl, 1,2,3-triazol-1-, 2-, or 4-yl, 1H-tetrazol-1- or 5-yl, 2H-tetrazol-2- or 5-yl, 2-, 3-, or 4-pyridyl, 2-, 4-, or 5-pyrimidinyl, 1-, 2-, 3-, 4-, 5-, 6-, or 7-indolyl, 2-, 3-, 4-, 5-, 6-, or 7-benzofuryl, 2-, 3-, 4-, 5-, 6-, or 7-benzothienyl, 1-, 2-, 4-, 5-, 6-, or 7-benzimidazolyl, 2-, 3-, 4-, 5-, 6-, 7-, or 8-quinolyl, and 1-, 3-, 4-, 5-, 6-, 7-, or 8-isoquinolyl, each optionally having substituent(s);

$R^{35}$ and $R^{36}$ are the same or different and each is an electron withdrawing group, provided that $R^{35}$ and $R^{36}$ are not the same groups; or $R^{34}$ and $R^{35}$ in combination form, together with the carbon atom they are bonded to, a ring having an electron withdrawing group and optionally having substituent(s), wherein the ring is optionally condensed with an aromatic hydrocarbon ring; and C**** an asymmetric carbon, or a salt thereof, which comprises adding a compound represented by the formula (IX):

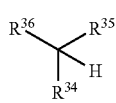

(IX)

wherein each symbol is as defined above, to a compound represented by the formula (VIII):

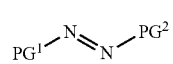

(VIII)

wherein each symbol is as defined above, in the presence of the compound of claim 1, a tautomer thereof or a salt thereof.

9. The method of claim 8, wherein $PG^1$ and $PG^2$ are the same or different and each is —$CO_2R^{37}$ or —$CONR^{38}R^{39}$ wherein $R^{37}$, $R^{38}$ and $R^{39}$ are the same or different and each is a lower alkyl group optionally having substituent(s), an aralkyl group optionally having substituent(s), an aryl group optionally having substituent(s) or a heteroaryl group selected from 2- or 3-thienyl, 2- or 3-furyl, 1-, 2-, or 3-pyrrolyl, 1-, 2-, 4-, or 5-imidazolyl, 2-, 4-, or 5-oxazolyl, 2-, 4-, or 5-thiazolyl, 1-, 3-, 4-, or 5-pyrazolyl, 3-, 4-, or 5-isoxazolyl, 3-, 4-, or 5-isothiazolyl, 1,2,4-triazol-1-, 3-, 4-, or 5-yl, 1,2,3-triazol-1-, 2-, or 4-yl, 1H-tetrazol-1- or 5-yl, 2H-tetrazol-2- or 5-yl, 2-, 3-, or 4-pyridyl, 2-, 4-, or 5-pyrimidinyl, 1-, 2-, 3-, 4-, 5-, 6-, or 7-indolyl, 2-, 3-, 4-, 5-, 6-, or 7-benzofuryl, 2-, 3-, 4-, 5-, 6-, or 7-benzothienyl, 1-, 2-, 4-, 5-, 6-, or 7-benzimidazolyl, 2-, 3-, 4-, 5-, 6-, 7-, or 8-quinolyl, and 1-, 3-, 4-, 5-, 6-, 7-, or 8-isoquinolyl, each optionally having substituent(s), or $R^{38}$ and $R^{39}$ in combination form, together with the nitrogen atom they are bonded to, a heterocycle selected from pyrrolidinyl, piperidinyl, morpholinyl, thiomorpholinyl, and piperazinyl, each optionally having substituent(s), wherein the heterocycle is optionally condensed with an aromatic hydrocarbon ring.

10. The method of claim 8, wherein $R^{35}$ and $R^{36}$ are the same or different and each is a cyano group, a nitro group, —$P(=O)R^{40}R^{41}$, —$SO_2R^{42}$, —$CO_2R^{43}$, —$CONR^{44}R^{45}$ or —$COR^{46}$ wherein $R^{40}$, $R^{41}$, $R^{42}$, $R^{43}$, $R^{44}$, $R^{45}$ and $R^{46}$ are the same or different and each is a hydrogen atom, a lower alkyl group optionally having substituent(s), an aralkyl group optionally having substituent(s), an aryl group optionally having substituent(s) or a heteroaryl group selected from 2- or 3-thienyl, 2- or 3-furyl, 1-, 2-, or 3-pyrrolyl, 1-, 2-, 4-, or 5-imidazolyl, 2-, 4-, or 5-oxazolyl, 2-, 4-, or 5-thiazolyl, 1-, 3-, 4-, or 5-pyrazolyl, 3-, 4-, or 5-isoxazolyl, 3-, 4-, or 5-isothiazolyl, 1,2,4-triazol-1-, 3-, 4-, or 5-yl, 1,2,3-triazol-1-, 2-, or 4-yl, 1H-tetrazol-1- or 5-yl, 2H-tetrazol-2- or 5-yl, 2-, 3-, or 4-pyridyl, 2-, 4-, or 5-pyrimidinyl, 1-, 2-, 3-, 4-, 5-, 6-, or 7-indolyl, 2-, 3-, 4-, 5-, 6-, or 7-benzofuryl, 2-, 3-, 4-, 5-, 6-, or 7-benzothienyl, 1-, 2-, 4-, 5-, 6-, or 7-benzimidazolyl, 2-, 3-, 4-, 5-, 6-, 7-, or 8-quinolyl, and 1-, 3-, 4-, 5-, 6-, 7-, or 8-isoquinolyl, each optionally having substituent(s), or $R^{44}$ and $R^{45}$ in combination form, together with the nitrogen atom they are bonded to, a heterocycle selected from pyrrolidinyl, piperidinyl, morpholinyl, thiomorpholinyl, and piperazinyl, each optionally having substituent(s), wherein the heterocycle is optionally condensed with an aromatic hydrocarbon ring.

11. The method of claim 8, wherein the ring having an electron withdrawing group and optionally having substituent(s) which is formed by $R^{34}$ and $R^{35}$ is cyclopentanone, cyclohexanone, 1-indanone or 1,2,3,4-tetrahydro-1-oxonaphthalene, each of which optionally has substituent(s).

* * * * *

UNITED STATES PATENT AND TRADEMARK OFFICE
CERTIFICATE OF CORRECTION

PATENT NO.        : 9,073,823 B2                                Page 1 of 1
APPLICATION NO.   : 13/828411
DATED             : July 7, 2015
INVENTOR(S)       : Takemoto et al.

It is certified that error appears in the above-identified patent and that said Letters Patent is hereby corrected as shown below:

In the claims:

Claim 7, column 38, line 28, "$C^{*}$ an asymmetric carbon," should read "$C^{*}$ is an asymmetric carbon,"

Claim 8, column 39, line 14, "$C^{*}$ an asymmetric carbon," should read "$C^{*}$ is an asymmetric carbon,"

Signed and Sealed this
First Day of March, 2016

Michelle K. Lee
*Director of the United States Patent and Trademark Office*